United States Patent
Anastasia et al.

(10) Patent No.: US 11,179,088 B2
(45) Date of Patent: Nov. 23, 2021

(54) ELECTROCARDIOGRAM ANALYSIS

(71) Applicant: J-WAVE DIAGNOSTICS S.R.L., Milan (IT)

(72) Inventors: Luigi Anastasia, Milan (IT); Ashton Boyd Christy, Milan (IT); Giuseppe Ciconte, Milan (IT); Edward Robert Grant, Milan (IT); Luke Robinson Melo, Milan (IT); Carlo Pappone, Milan (IT)

(73) Assignee: J-WAVE DIAGNOSTICS S.R.L., Milan (IT)

(*) Notice: Subject to any disclaimer, the term of this patent is extended or adjusted under 35 U.S.C. 154(b) by 0 days.

(21) Appl. No.: 17/225,410

(22) Filed: Apr. 8, 2021

(65) Prior Publication Data

US 2021/0315506 A1    Oct. 14, 2021

Related U.S. Application Data

(60) Provisional application No. 63/007,496, filed on Apr. 9, 2020.

(30) Foreign Application Priority Data

Apr. 9, 2020 (EP) .................................. 20169028

(51) Int. Cl.
*A61B 5/28* (2021.01)
*A61B 5/00* (2006.01)
*A61B 5/352* (2021.01)
*G16H 50/20* (2018.01)

(52) U.S. Cl.
CPC ............ *A61B 5/352* (2021.01); *A61B 5/7264* (2013.01); *A61B 5/7267* (2013.01); *G16H 50/20* (2018.01)

(58) Field of Classification Search
CPC ....... A61B 5/0245; A61B 5/318; A61B 5/349; A61B 5/352; A61B 5/7264; G16H 50/70
See application file for complete search history.

(56) References Cited

U.S. PATENT DOCUMENTS

2019/0059763 A1    2/2019   Shakur et al.

OTHER PUBLICATIONS

Extended European Search Report issued on European Application 20169028.6, dated Sep. 7, 2020, 7 pages.

*Primary Examiner* — Jon Eric C Morales
(74) *Attorney, Agent, or Firm* — Leber IP Law; Sarah M. Gates

(57) ABSTRACT

A computer-implemented method of facilitating electrocardiogram ("ECG") analysis involves receiving one or more sensed ECG traces for a patient, each of the sensed ECG traces representing sensed patient heart activity over a sensed time period, and, for each of the one or more sensed ECG traces: identifying a plurality of corresponding sensed ECG trace segments, each of the sensed ECG trace segments representing sensed patient heart activity for the patient over a segment of the sensed time period, and determining a representative ECG trace based on at least one of the identified corresponding sensed ECG trace segments. The method involves causing at least one neural network classifier to be applied to the one or more determined representative ECG traces to determine one or more diagnostically relevant scores related to at least one diagnosis of the patient. Other methods, systems, and computer readable media are disclosed.

24 Claims, 24 Drawing Sheets

1040

Representative training ECG trace record

| | |
|---|---|
| Patient ID | 8f3af58e... |
| Lead ID | 1 |
| ECG voltage 1 | 0 |
| ECG voltage 2 | 22 |
| ... | ... |
| ECG voltage 1500 | 239 |

ELECTROCARDIOGRAM ANALYSIS

RELATED APPLICATIONS

This application claims the benefit of U.S. Provisional Application No. 63/007,496 filed on Apr. 9, 2020, and European Application No. 20169028.6, filed on Apr. 9, 2020, all of which are hereby incorporated by reference in their entireties.

BACKGROUND

1. Field

Embodiments of this invention relate to electrocardiogram analysis and more particularly to computer implemented facilitating of analysis of electrocardiograms.

2. Description of Related Art

Electrocardiogram ("ECG") analysis may be used in pathology to help in providing diagnosis of syndromes, diseases, and/or disorders. Known ECG analysis systems may include machines configured to provide generally raw ECG depictions and may require an expert to review and analyze the raw ECGs and to rely on their professional judgment alone to come to a diagnosis. However, even experts cannot identify some subtle properties of raw ECG traces, as provided by some known ECG analysis systems that may be indicative of particular diagnoses. Further, access to experts may be limited and/or costly and the use of experts alone with known ECG systems may provide inconsistent diagnosis results. In particular, for some syndromes, diseases, and/or disorders, such as, for example, Brugada Syndrome analysis, a raw ECG displayed by some known systems may be diagnostic only in about one third of the patients. The remaining two thirds of the patients may possess a very subliminal ECG abnormalities, which may not be detectable by the human eye viewing the raw ECGs provided by some known systems. Further, to unmask a diagnostic ECG pattern for BrS, some known ECG diagnostic approaches require the use of drugs by the patient before an expert reviews raw ECG traces, which may enhance the ECG abnormalities intrinsic of the disease, but may introduce dangers to the patients. In fact, some of these drugs may have potential pro-arrhythmic effects, which may cause life threatening arrhythmias during the test. Accordingly, some known ECG systems may result in slow, costly, unsafe, and/or inaccurate diagnoses.

SUMMARY

In accordance with various embodiments, there is provided a computer-implemented method of facilitating electrocardiogram ("ECG") analysis. The method involves receiving one or more sensed ECG traces for a patient, each of the sensed ECG traces representing sensed patient heart activity over a sensed time period, and, for each of the one or more sensed ECG traces: identifying a plurality of corresponding sensed ECG trace segments, each of the sensed ECG trace segments representing sensed patient heart activity for the patient over a segment of the sensed time period, and determining a representative ECG trace based on at least one of the identified corresponding sensed ECG trace segments. The method involves causing at least one neural network classifier to be applied to the one or more determined representative ECG traces to determine one or more diagnostically relevant scores related to at least one diagnosis of the patient.

Determining the representative ECG trace may involve identifying a subset of the plurality of corresponding sensed ECG trace segments, the subset excluding at least one of the plurality of corresponding sensed ECG trace segments, and determining the representative ECG trace based on the identified subset.

Identifying the subset of the plurality of corresponding sensed ECG trace segments may involve applying principal component analysis to the plurality of corresponding sensed ECG trace segments to determine a respective set of principal component scores associated with each of the corresponding sensed ECG trace segments, and comparing the principal component scores to identify the at least one of the plurality of corresponding sensed ECG trace segments to be excluded from the subset.

Each of the sets of principal component scores may include a first principal component score and a second principal component score. Comparing the principal component scores may involve determining a first confidence limit and a second confidence limit from the first and second principal component scores respectively, and for each of the corresponding sensed ECG trace segments, comparing the first and second principal component scores associated with the sensed ECG trace segment to the first and second confidence limits.

Comparing the first and second principal component scores associated with the sensed ECG trace segment to the first and second confidence limits may involve determining whether the first and second principal component scores are outside of an ellipse having a radius set by the first and second confidence limits, and if so, identifying the sensed ECG trace segment to be excluded from the subset.

Determining the first and second confidence limits may involve applying the Hotelling $T^2$ statistic to the first and second principal component scores respectively.

Applying the Hotelling $T^2$ statistic to the first and second principal component scores may involve using the critical value of the F-distribution at at least about 95% confidence.

Determining the representative ECG trace based on the at least one of the identified corresponding sensed ECG trace segments may involve averaging the corresponding sensed ECG trace segments included in the subset.

Identifying the plurality of corresponding sensed ECG trace segments may involve identifying respective common features in the sensed ECG trace segments and identifying respective start and end times for each of the plurality of sensed ECG trace segments relative to the identified common features.

Identifying the respective common features may involve identifying respective R peaks in each of the sensed ECG trace segments.

The method may involve producing signals representing the one or more diagnostically relevant scores for causing at least one display to display a representation of the one or more diagnostically relevant scores.

The at least one neural network classifier may include a BrS neural network classifier.

The method may involve training the at least one neural network classifier, the training involving receiving a plurality of sets of training ECG traces, wherein each set of the sets of training ECG traces represents sensed heart activity over a training time period for a respective associated training patient of a plurality of training patients, receiving, for each set of the plurality of sets of training ECG traces, a respective diagnosis for the training patient associated with the set of training ECG traces, and, for each of the training ECG traces: identifying a plurality of corresponding training ECG trace segments, each of the training ECG trace segments representing patient heart activity over a segment of the training time period, and determining a representative training ECG trace based on at least one of the identified corresponding training ECG trace segments. The training may involve causing the at least one neural network classifier to be trained using the representative training ECG traces and the diagnoses.

In accordance with various embodiments, there is provided a computer-implemented method of facilitating electrocardiogram ("ECG") analysis, the method involving receiving a plurality of sets of training ECG traces, wherein each set of the sets of training ECG traces represents sensed heart activity over a training time period for a respective associated training patient of a plurality of training patients, receiving, for each set of the plurality of sets of training ECG traces, a respective diagnosis for the training patient associated with the set of training ECG traces, and, for each of the training ECG traces: identifying a plurality of corresponding training ECG trace segments, each of the training ECG trace segments representing patient heart activity over a segment of the training time period, and determining a representative training ECG trace based on at least one of the identified corresponding training ECG trace segments. The method involves causing at least one neural network classifier to be trained using the representative training ECG traces and the diagnoses, the at least one neural network classifier configured to output one or more diagnostically relevant scores related to at least one diagnosis.

Determining the representative training ECG trace may involve identifying a subset of the plurality of corresponding training ECG trace segments, the subset excluding at least one of the plurality of corresponding training ECG trace segments, and determining the representative training ECG trace based on the identified subset.

Identifying the subset of the plurality of corresponding training ECG trace segments may involve applying principal component analysis to the plurality of corresponding training ECG trace segments to determine a respective set of principal component scores associated with each of the corresponding training ECG trace segments, and comparing the principal component scores to identify the at least one of the plurality of corresponding training ECG trace segments to be excluded from the subset.

Each of the sets of principal component scores may include a first principal component score and a second principal component score and comparing the principal component scores may involve determining a first confidence limit and a second confidence limit from the first and second principal component scores respectively, and, for each of the corresponding training ECG trace segments, comparing the first and second principal component scores associated with the training ECG trace segment to the first and second confidence limits.

Comparing the first and second principal component scores associated with the training ECG trace segment to the first and second confidence limits may involve determining whether the first and second principal component scores are outside of an ellipse having a radius set by the first and second confidence limits, and if so, identifying the training ECG trace segment to be excluded from the subset.

Determining the first and second confidence limits may involve applying a Hotelling $T^2$ statistic equation to the first and second principal component scores respectively.

Applying the Hotelling $T^2$ statistic equation to the first and second principal component scores may involve using the critical value of the F-distribution at at least about 95% confidence.

Determining the representative ECG trace based on the at least one of the identified corresponding training ECG trace segments comprises averaging the corresponding training ECG trace segments included in the subset.

Identifying the plurality of corresponding training ECG trace segments may involve identifying respective common features in the training ECG trace segments and identifying respective start and end times for each of the plurality of training ECG trace segments relative to the identified common features.

Identifying the respective common features may involve identifying respective R peaks in each of the training ECG trace segments.

The at least one neural network classifier may include a BrS neural network classifier and wherein each of the diagnoses received includes a BrS diagnoses.

In accordance with various embodiments, there is provided a system for facilitating electrocardiogram ("ECG") analysis comprising at least one processor configured to perform any of the above methods.

In accordance with various embodiments, there is provided a non-transitory computer readable medium having stored thereon codes which when executed by at least one processor cause the at least one processor to perform any of the above methods.

BRIEF DESCRIPTION OF THE DRAWINGS

In drawings which illustrate embodiments of the invention.

DETAILED DESCRIPTION

Cardiovascular mortality has decreased in the past 30 years owing to a growing recognition of dietary and lifestyle measures that improve heart health. Despite this progress, the problem of cardiovascular disease persists, causing 17 million deaths per year world-wide. Approximately one-quarter of these fatalities occur as an unexpected loss of heart function known as sudden cardiac death (SCD). SCD can occur without warning in the absence of a preexisting cardiac disease. As many as one-third of these deaths occur as manifestations of symptomatic or asymptomatic cardiogenetic condition known as Brugada Syndrome (BrS).

Medical practitioners commonly rely on Electrocardiogram (ECG) analysis as a pathological tool to classify ECG waveforms as an aid in diagnosing cardiac syndromes, diseases, and/or disorders. Unfortunately, the raw ECG of a patient, as provided by some known systems, presents as diagnostic for BrS in fewer than twenty percent of cases. The remaining BrS positive individuals may show a wide spectrum of ECG abnormalities. Moreover, as many as half of BrS patients surviving to a cardiac arrest present what appears to be a completely normal ECG to a medical professional. As a consequence, most BrS individuals remain undiagnosed.

Even for symptomatic patients, known ECG analysis techniques require an expert to review and analyze raw ECGs and to use their professional judgment to reach a diagnosis. However, observation by experts sometimes cannot identify some subtle properties of raw ECG traces that may be indicative of particular diagnoses. Access to experts may be limited and/or costly, and a reliance on any individual to recognize non-obvious patterns in an ECG could well yield inconsistent diagnosis results. Moreover, use of some known ECG systems may result in slow, costly, unsafe, and/or inaccurate diagnoses.

Accordingly, to unmask a Brugada ECG pattern and obtain an accurate diagnosis of the state of a patient with a BrS family history usually requires the administration of a sodium-channel blocker drug that induces ECG abnormalities intrinsic to the disease. However, such drugs may cause life-threatening arrhythmias, which means that this method of diagnosis can only be administered in a suitably equipped operating room.

These safety issues greatly limit the general applicability of the current diagnostic systems, ultimately exposing undiagnosed BrS subjects to the risk of SCD.

Figure 1:
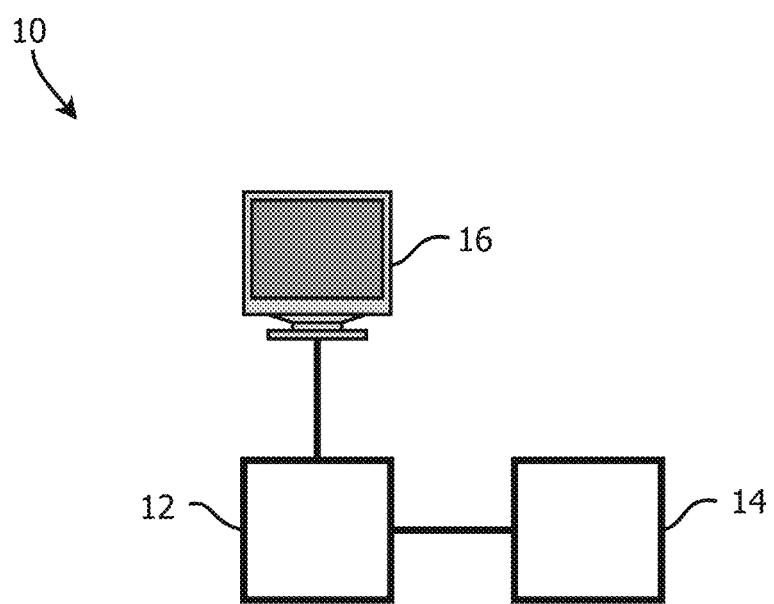
FIG. 1 is a schematic view of a system for facilitating electrocardiogram ("ECG") analysis or classification according to various embodiments.

Referring to FIG. 1, there is provided a system 10 for facilitating electrocardiogram ("ECG") analysis or classification, in accordance with various embodiments. The system 10 includes a computer-implemented ECG analyzer 12 in communication with an ECG data source 14 and a display 16.

In various embodiments, the system 10 may be configured to use ECG data to aid in the diagnosis BrS. However, in various embodiments, the system 10 or a system generally similar to the system 10 may be used to aid in the diagnosis of one or more syndromes, disorders and/or primary electrical diseases such as Brugada syndrome (BrS), early repolarization syndrome (ERS), long QT syndrome (LQTS), short QT syndrome (SQTS), and/or other analytic, possibly idiopathic disorders. In some embodiments, a diagnosis may be reached through use of the system 10 along with other diagnostic techniques. For example, in some embodiments, the system 10 may be used to provide a non-invasive screening program. In various embodiments, such a non-invasive screening test for BrS could save one million lives per year.

In some embodiments, the system 10 may include features that facilitate diagnosis of one or more syndromes, diseases, and/or disorders such as BrS from ECG data without using medication to elicit the ECG response. For example, in some embodiments, the system 10 may facilitate a diagnosis of BrS from ECG data without requiring a patient to use drugs such as a sodium channel blocker agent (e.g., ajmaline, flecainide, pilsicainide, or procainamide). Accordingly, the system 10 may facilitate a computer-assisted method for non-invasive diagnosis of BrS or an indication of the possibility of BrS from ECG data without the use of a potentially lethal drug.

In some embodiments described herein, the system 10 may be configured to aid in the diagnosis of BrS from patterns in conventional ECG trace data recognized by a deep-learning model trained with ECG data. In various embodiments, the system 10 may be suitable for integration in current and future generations of ECG recording devices, which may enable them to provide an automated, operator independent, diagnosis. In some embodiments, ECG signals from various medical devices (including implantable and wearable devices as well as stationary and portable clinical and home monitors) may suffice for the system to facilitate diagnosis and/or recognition of arrhythmia signals associated with BrS or other arrhythmogenic cardiomyopathy. In some embodiments, the system 10 may be configured to process ECG signals produced by consumer-wearable devices, such as smartwatches, smartphones, and/or other multipurpose electronic products for aiding in the diagnosis of BrS and/or other hidden arrhythmic pathologies.

Referring to FIG. 1, in various embodiments, the ECG data source 14 may be configured to provide to the ECG analyzer 12, ECG data representing one or more sensed ECG traces for a patient, each of the sensed ECG traces representing sensed patient heart activity over a sensed time period. For example, in some embodiments, the ECG data source 14 may include an ECG sensor system configured to capture the ECG data using sensors or leads coupled to the patient. In some embodiments, for example, the ECG data source 14 may include 12 leads coupled to the patient and configured to sense ECG data and so the ECG data may represent 12 sensed ECG traces for the patient. In various embodiments, alternative numbers of leads and/or ECG traces may be used.

The ECG analyzer 12 may receive the ECG data representing the one or more sensed ECG traces for the patient from the ECG data source 14. In some embodiments, the ECG analyzer 12 may store the ECG data in memory.

The ECG analyzer 12 may then, for each of the one or more sensed ECG traces, identify a plurality of corresponding sensed ECG trace segments, each of the sensed ECG trace segments representing sensed patient heart activity for the patient over a segment of the sensed time period, and determine a representative ECG trace based on at least one of the identified corresponding sensed ECG trace segments. In some embodiments, the sensed ECG trace segments may be chosen such that each ECG trace segment represents sensed ECG data for a single heartbeat. In various embodiments, each of the ECG trace segments may be generally similar, having repeated features.

In various embodiments, identifying sensed ECG trace segments that correspond to one another and may be generally similar and then determining the representative ECG trace based on the identified ECG trace segments may help the ECG analyzer 12 to cause the representative ECG trace to represent features that are repeated in the ECG trace segments, reducing distortion caused by noise and/or aberration, arising, for example, from electrical interference or unrelated patient motion.

In some embodiments, the ECG analyzer 12 may identify the trace segments by identifying common features in the sensed ECG trace segments and identifying respective start and end times for each of the plurality of sensed ECG trace segments relative to the identified common features. In some embodiments, for example, the ECG analyzer 12 may identify an R peak for each trace segment and identify start and end times for the trace segment relative to the identified R peak. In various embodiments, identifying common features, such as an R peak, for each trace segment may allow the ECG analyzer 12 to line up or sync the ECG trace segments so that the ECG trace segments can be compared regardless of the start time for each ECG trace segment. In various embodiments, this may facilitate determining a representative ECG trace that better reflects common features included in the ECG trace segments.

In some embodiments, the ECG analyzer 12 may use only a subset of the ECG trace segments included in each trace to determine or generate the representative ECG traces. In some embodiments, for example, the ECG analyzer 12 may disregard ECG trace segments that are considered to represent outlier ECG information compared to the other ECG trace segments. In various embodiments, by using only a subset of the ECG trace segments to determine the representative ECG traces, the ECG analyzer 12 may obtain representative ECG traces that are generated without considering abnormal ECG trace segments and this may result in the representative ECG traces being better indicators of repeated features in the ECG trace segments. In various embodiments, this may facilitate more accurate scores and/or indications provided by the system 10 that may be used to aid in diagnoses.

In some embodiments, the ECG analyzer 12 may determine the representative ECG trace by averaging ECG trace segments. In various embodiments, by averaging ECG trace segments, effects of repeated features in the segments may be emphasized whereas the effects of anomalous features of the segments may be minimized.

In various embodiments, the one or more sensed ECG traces may include 12 sensed ECG traces and so the ECG analyzer 12 may determine 12 representative ECG traces. The ECG analyzer 12 may store the determined representative ECG traces in memory. In various embodiments, each of the 12 representative ECG traces may represent repeated features in the 12 sensed ECG traces. In some embodiments, because of the processing performed by the ECG analyzer 12 in determining the 12 representative ECG traces, these traces may act as excellent inputs for a neural network classifier or function in determining a diagnostically relevant score for the patient.

In various embodiments, the ECG analyzer 12 may cause at least one neural network classifier or function to be applied to the one or more determined representative ECG traces to determine one or more diagnostically relevant scores related to the diagnosis of the patient. For example, in some embodiments, the ECG analyzer 12 may have stored therein data defining a BrS diagnosis neural network classifier, which may be configured to include in its input, 12 representative ECG traces, and to output a diagnosis score, such as a BrS diagnosis score. In some embodiments, the diagnosis score may be a statistical representation of the computer-determined confidence in a machine diagnosis of a disease and/or disorder. For example, in some embodiments, the ECG analyzer 12 may be configured to cause the BrS diagnosis neural network classifier to output the BrS diagnosis score as a decimal number between 0 and 1 with scores near 0 representing high confidence of a negative diagnosis of BrS (i.e., the patient does not have BrS) and scores near 1 representing high confidence of a positive diagnosis of BrS (i.e., the patient does have BrS), and scores in between representing varying levels of confidence. In some embodiments, the one or more diagnostically relevant scores may represent a disease state classifier score which may be used to classify the patient as within a particular disease state.

In some embodiments, the ECG analyzer 12 may cause the BrS diagnosis neural network classifier to be applied to the 12 representative ECG traces, previously determined, to determine the BrS diagnosis score. The ECG analyzer 12 may store the BrS diagnosis score in memory.

In some embodiments, the ECG analyzer 12 may produce signals representing the one or more diagnostically relevant scores for causing a representation of the scores to be displayed by the display 16. For example, in some embodiments, the ECG analyzer 12 may produce signals for causing a number between 0 and 1 representing the score, which may be representative of a diagnostic probability, for example, to be displayed on the display 16.

In some embodiments, the display 16 may be viewed by the patient and/or a medical professional. In various embodiments, action may be taken based on the displayed representation of the diagnostically relevant score, which may help to prevent future life-threatening events. For example, a BrS diagnosis score indicating a high likelihood of the patient having BrS, may cause a physician to perform or modify further diagnostic and/or therapeutic procedures.

In some embodiments, the ECG analyzer 12 may be configured to generate signals based on the one or more diagnostically relevant scores for causing the function of an external or implantable defibrillator or cardiac pacemaker to be regulated.

In some embodiments, the display 16 and/or any or all of the system 10 may be included in the surgical theatre to facilitate enhanced monitoring of diagnostic or therapeutic procedures for a patient in the surgical theatre for the purpose of monitoring diagnostic and therapeutic procedures, including an enhanced monitoring of diagnostic drug dose-response or of the therapeutic outcome following interventional procedures, including catheter ablation, for example.

In some embodiments, the display 16 and/or any or all of the system 10 may be included in a continuous cardiac monitoring system to facilitate detection of primary electronic disorder arrhythmias in ambulatory or sedentary patients, for example.

In some embodiments, the display 16 and/or any or all of the system 10 may be included in a continuous cardiac monitoring system to facilitate alerting of appropriate responders of overnight primary electronic disorder arrhythmias.

In various embodiments, the display 16 and/or any or all of the system 10 may be included in various alternative or additional environments for alerting a patient to the determined one or more diagnostically relevant scores.

ECG Analyzer—Processor Circuit

Figure 2:
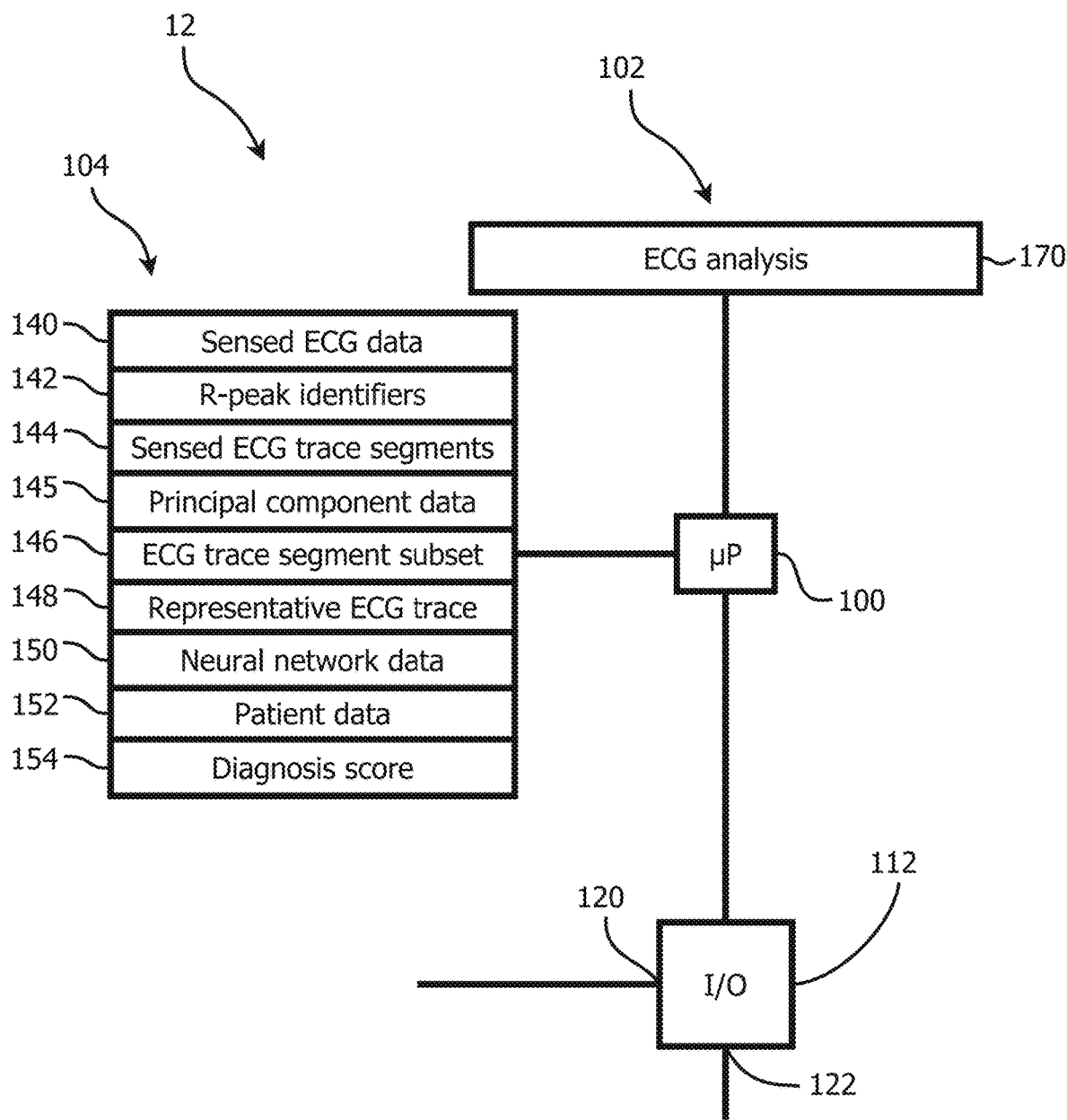
FIG. 2 is a schematic view of an ECG analyzer of the system shown in FIG. 1 including a processor circuit in accordance with various embodiments.

Referring now to FIG. 2, a schematic view of the ECG analyzer 12 of the system 10 shown in FIG. 1 according to various embodiments is shown. Referring to FIG. 2, the ECG analyzer 12 includes a processor circuit including an analyzer processor 100 and a program memory 102, a storage memory 104, and an input/output (I/O) interface 112, all of which are in communication with the analyzer processor 100. In various embodiments, the analyzer processor 100 may include one or more processing units, such as for example, a central processing unit (CPU), a graphical processing unit (GPU), and/or a field programmable gate array (FPGA). In some embodiments, any or all of the functionality of the ECG analyzer 12 described herein may be implemented using one or more FPGAs.

The I/O interface 112 includes an interface 120 for communicating with the ECG data source 14 and an interface 122 for communicating with the display 16. In some embodiments, the I/O interface 112 may also include an additional interface for facilitating networked communication through a network such as the Internet. In some embodiments, any or all of the interfaces 120 and/or 122 may facilitate a wireless or wired communication. In some embodiments, each of the interfaces shown in FIG. 2 may include one or more interfaces and/or some or all of the interfaces included in the I/O interface 112 may be implemented as combined interfaces or a single interface.

In some embodiments, where a device is described herein as receiving or sending information, it may be understood that the device receives signals representing the information via an interface of the device or produces signals representing the information and transmits the signals to the other device via an interface of the device.

Processor-executable program codes for directing the analyzer processor 100 to carry out various functions are stored in the program memory 102. Referring to FIG. 2, the program memory 102 includes a block of codes 170 for directing the ECG analyzer 12 to perform facilitating ECG analysis functions. In this specification, it may be stated that certain encoded entities such as applications or modules perform certain functions. Herein, when an application, module or encoded entity is described as taking an action, as part of, for example, a function or a method, it will be understood that at least one processor (e.g., the analyzer processor 100) is directed to take the action by way of programmable codes or processor-executable codes or instructions defining or forming part of the application.

The storage memory 104 includes a plurality of storage locations including location 140 for storing sensed ECG data, location 142 for storing R-peak identifier data, location 144 for storing sensed ECG trace segment data, location 145 for storing principal component data, location 146 for storing ECG trace segment subset data, location 148 for storing representative ECG trace data, location 150 for storing neural network data, location 152 for storing patient data, and location 154 for storing diagnosis score data. In various embodiments, the plurality of storage locations may be stored in a database in the storage memory 104.

In various embodiments, the block of codes 170 may be integrated into a single block of codes or portions of the block of code 170 may include one or more blocks of code stored in one or more separate locations in the program memory 102. In various embodiments, any or all of the locations 140-154 may be integrated and/or each may include one or more separate locations in the storage memory 104.

Each of the program memory 102 and storage memory 104 may be implemented using one or more storage devices including random access memory (RAM), a hard disk drive (HDD), a solid-state drive (SSD), a network drive, flash memory, a memory stick or card, any other form of non-transitory computer-readable memory or storage medium, and/or a combination thereof. In some embodiments, the program memory 102, the storage memory 104, and/or any portion thereof may be included in a device separate from the ECG analyzer 12 and in communication with the ECG analyzer 12 via the I/O interface 112, for example. In some embodiments, the functionality of the analyzer processor 100 and/or the ECG analyzer 12 as described herein may be implemented using a plurality of processors and/or a plurality of devices, which may be distinct devices which are in communication via respective interfaces and/or a network, such as the Internet, for example.

ECG Analyzer Operation

Figure 3:
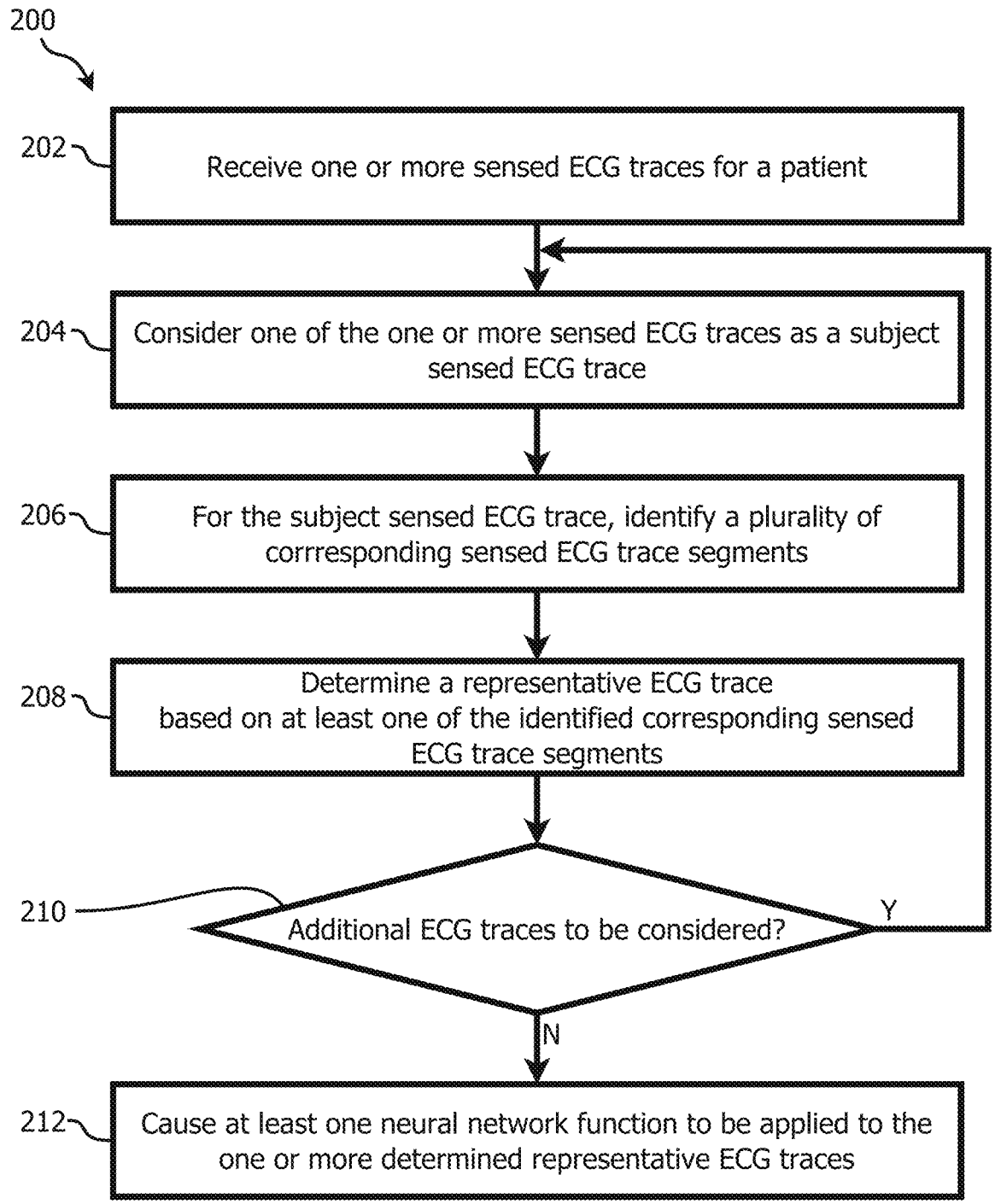
FIG. 3 is a flowchart depicting blocks of code for directing the ECG analyzer of the system shown in FIG. 1 to perform facilitating ECG analysis functions in accordance with various embodiments.

As discussed above, in various embodiments, the ECG analyzer 12 shown in FIGS. 1 and 2 may be configured to facilitate ECG analysis. Referring to FIG. 3, a flowchart depicting blocks of code for directing the analyzer processor 100 shown in FIG. 2 to perform facilitating ECG analysis functions in accordance with various embodiments is shown generally at 200. The blocks of code included in the flowchart 200 may be encoded in the block of codes 170 of the program memory 102 shown in FIG. 2, for example.

Referring to FIG. 3, the flowchart 200 begins with block 202 which directs the analyzer processor 100 to receive one or more sensed ECG traces for a patient, each of the sensed ECG traces representing sensed patient heart activity over a sensed time period.

In some embodiments, the ECG data source 14 may include an ECG monitor or sensor system including 12 leads coupled to the patient. The 12 leads may be located on the patient to provide tracing from 12 different electrical positions of the patient's heart. In some embodiments, for example, the 12 leads may include three bipolar limb leads, 3 unipolar limb leads, and six unipolar chest leads. In various embodiments, each of the 12 leads may sense voltage as the patient's heart beats. A representation of the sensed voltage over time may be considered as a sensed ECG trace. In some embodiments, the ECG data source 14 may generate and/or store a respective sensed ECG trace record, an exemplary representation of which is shown at 260 in FIG. 4, for each of the 12 sensed ECG traces.

Figure 4:
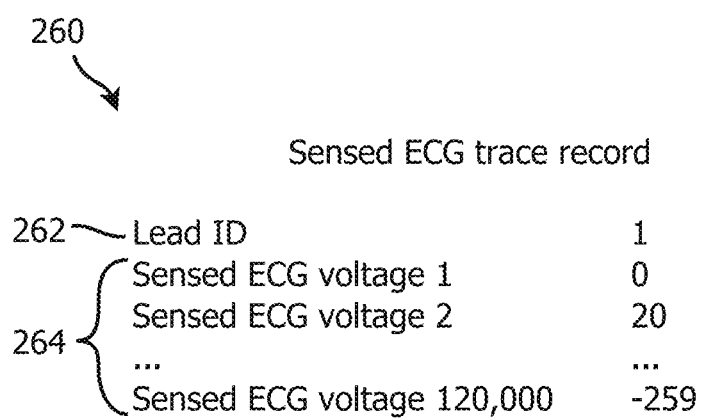
FIG. 4 is a representation of an exemplary sensed ECG trace record that may be used in the system shown in FIG. 1 in accordance with various embodiments.

Referring to FIG. 4, in some embodiments, the ECG trace record 260 may include a lead identifier field 262 for storing a lead identifier for identifying the lead from which the ECG trace was sensed and sensed ECG voltage fields 264, each of which stores a value representing a voltage sensed at a particular time. In some embodiments, each of the sensed ECG voltage fields 264 may be associated with a respective time, for example, based on an order or position of the sensed ECG voltage field in the ECG trace record 260. In some embodiments, for example, the sensed ECG voltage fields 264 may represent voltages measured at 2000 Hz or 0.5 ms apart and so a first sensed ECG voltage field may be associated with a time of 0 ms and each subsequent sensed ECG voltage field may be associated with respective times at increments of 0.5 ms later. In various embodiments alternative sampling frequencies may be used, such as, for example 500 Hz, or another frequency that may facilitate meaningful representation of features of a heartbeat. In some embodiments, the sensed ECG voltage fields 264 of the ECG trace record 260 may represent voltages over a time period spanning a selected duration of a measurement. In some embodiments, the duration of measurement may be chosen by an operator of the ECG data source 14 and/or the ECG analyzer 12. In some embodiments, the time period may be about 60 seconds, for example. In some embodiments, other time periods for the sensed ECG trace record 260 may be used, such that reliable output may be provided. For example, in some embodiments, the time period may be about 10-20 seconds, 20-30 seconds, or a few seconds.

In some embodiments, the sensed ECG voltage fields 264 may store integer values which represent steps of 0.0001 mV, such that the integer values may be converted to measured mV by dividing by 10,000.

Referring back to FIG. 3, block 202 may direct the analyzer processor 100 to receive representations of 12 sensed ECG trace records, each having generally similar format to the sensed ECG trace record 260 shown in FIG. 3 and to store the sensed ECG trace records in the location 140 of storage memory 104. In some embodiments, for example, block 202 may direct the analyzer processor 100 to receive the representations of the sensed ECG trace records via the interface 120 of the I/O interface 112 shown in FIG. 2. In some embodiments, block 202 may direct the analyzer processor 100 to store the sensed ECG trace records using an SQL database, for example.

Referring to FIG. 3, after block 202 has been executed, the analyzer processor 100 may proceed to blocks 204, 206, and 208, which may direct the analyzer processor 100 to consider one of the sensed ECG traces, to segment the considered ECG trace, and to determine a representative ECG trace based on at least one of the segments. In various embodiments, blocks 204, 206, and 208 may be executed for each of the one or more sensed ECG traces received at block 202, such that a representative ECG trace is determined for each of the sensed ECG traces received.

Block 204 directs the analyzer processor 100 to consider one of the one or more sensed ECG traces as a subject sensed ECG trace. For example, in some embodiments, on a first execution of block 204, block 204 may direct the analyzer processor 100 to consider the sensed ECG trace represented by the sensed ECG trace record 260 shown in FIG. 4 as the subject sensed ECG trace.

Referring to FIG. 3, block 206 then directs the analyzer processor 100 to, for the subject sensed ECG trace, identify a plurality of corresponding sensed ECG trace segments, each of the sensed ECG trace segments representing sensed patient heart activity for the patient over a segment of the sensed time period. In some embodiments, block 206 may direct the analyzer processor 100 to identify segments of the sensed ECG trace as sensed ECG trace segments. In some embodiments, the sensed ECG trace segments may be identified such that they generally include similar or repeated features. In some embodiments, block 204 may direct the analyzer processor 100 to store representations of the sensed ECG trace segments in the location 144 of the storage memory 104.

Figure 5:
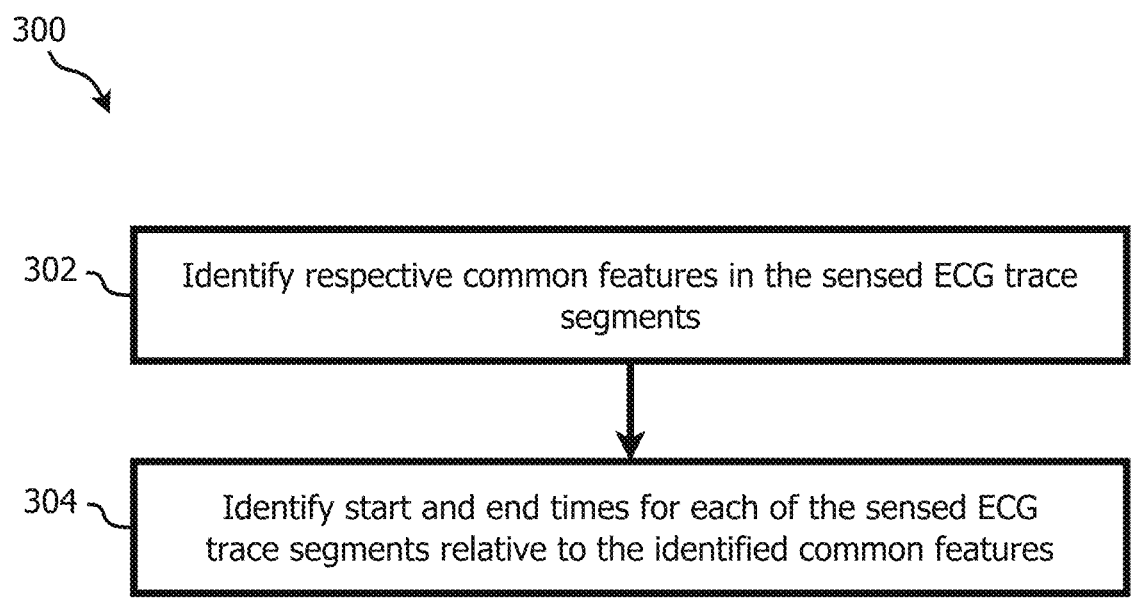
FIG. 5 is a flowchart depicting blocks of code that may be included in the blocks of code shown in FIG. 3 in accordance with various embodiments.

Referring to FIG. 5, there is shown a flowchart 300 depicting blocks of code that may be included in the block 206 shown in FIG. 3, in various embodiments. The flowchart 300 begins with block 302 which directs the analyzer processor 100 to identify respective common features in the sensed ECG trace segment.

In some embodiments, block 302 may direct the analyzer processor 100 to first process the information represented by the sensed ECG trace record 260 to conform to a designated format. For example, in some embodiments, block 302 may direct the analyzer processor 100 to apply denoising and background suppression to the sensed ECG trace record using a Fourier analysis and/or another form of harmonic analysis, coupled with one or more infinite impulse response filters, and/or other digital filters.

In some embodiments, the common features identified may be an R-peak for each of the sensed ECG trace segments and block 302 may direct the analyzer processor 100 to identify a respective R-peak in each of the sensed ECG trace segments. In some embodiments, block 302 may direct the analyzer processor 100 to apply a wavelet decomposition algorithm, such as discrete, continuous, undecimated, stationary, or maximal overlap discrete wavelet transforms, to detect temporal positions of QRS complexes represented by the sensed ECG trace record 260, a QRS complex being the combination of three of the graphical deflections seen on a typical ECG trace. The QRS complex may be the central and most visually obvious part of the tracing (i.e., the main spike seen on an ECG line). The QRS complex may correspond to the depolarization of the right and left ventricles of the human heart and contraction of the large ventricular muscles.

In various embodiments, block 302 may direct the analyzer processor 100 to store time identifiers representing temporal position of respective R-peaks for each detected QRS complex, in the location 142 of the storage memory 104. For example, in some embodiments, block 302 may direct the analyzer processor 100 to store an R-peak identifier record 340 as shown in FIG. 6 in the location 142 of the storage memory 104.

Figure 6:
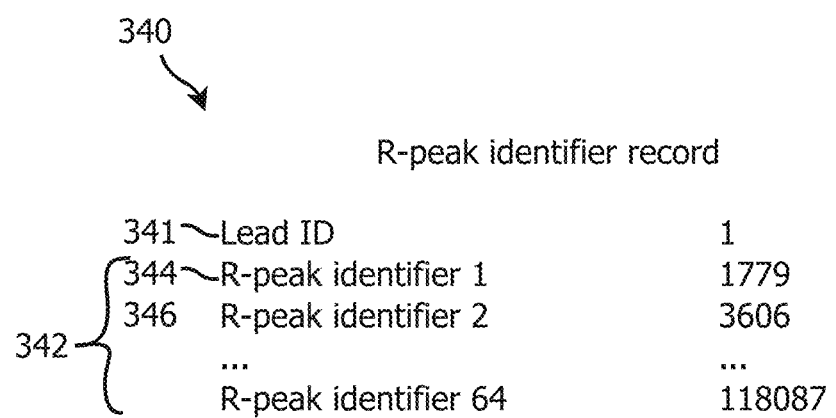
FIG. 6 is a representation of an exemplary R-peak identifier record that may be used in the system shown in FIG. 1 in accordance with various embodiments.

Referring to FIG. 6, the R-peak identifier record 340 includes a lead identifier field 341 for storing a lead identifier for identifying the lead from which the ECG trace was sensed and R-peak identifier fields 342 for storing temporal identifiers identifying times or temporal positions for each identified R-peak from the sensed ECG trace record 260 shown in FIG. 4. For example, referring to FIG. 6, the R-peak identifier record 340 includes a first R-peak identifier field 344 storing an integer value that identifies a position within the sensed ECG trace record 260 that corresponds to a first identified R-peak. In some embodiments, the first R-peak identifier field 344 storing a value of 1779 indicates that the 1779th sensed ECG voltage field of the sensed ECG trace record 260 represents a voltage associated with an R-peak. The second R-peak identifier field 346 storing a value of 3606 indicates that the 3606th sensed ECG voltage field of the sensed ECG trace record 260 represents a voltage associated with an R-peak.

Block 304 then directs the analyzer processor 100 to identify respective start and end times for each of the plurality of sensed ECG trace segments relative to the identified common features. In some embodiments, block 304 may direct the analyzer processor 100 to segment the sensed ECG trace record into canonical temporal windows based on the R-peak identifiers, with each segment window centered on the R-peak of the QRS complex. In various embodiments, the temporal length of a window may have been previously set and stored in storage memory 104, for example. In some embodiments, for example, the temporal length of a window may be set to a time such that features included in the window, centred around the R-peak of an ECG trace segment, would provide enough information for a particular diagnosis neural network classifier to output a particular diagnosis score such as for example a BrS diagnosis, enabling, for example, a BrS diagnosis neural network classifier to output the BrS diagnosis score. In various embodiments, for example, the temporal length of the window may be about 750 ms or about 1,500 ECG trace data points at a sampling rate of 2000 Hz. In some embodiments, the temporal length may have been empirically determined to serve adequately to capture a heartbeat without overlapping adjacent ones.

In various embodiments, block 304 may direct the analyzer processor 100 to identify the start and end times by subtracting and adding, respectively, half of the temporal length of the window from each R-peak identifier. For example, in some embodiments, the start time for the R-peak identified by the first R-peak identifier field 344 shown in FIG. 6 may be identified as 1779−(1500/2)=1029, and the end time for the R-peak identified by the first R-peak identifier field 344 may be identified as 1779+(1500/2)=2529. Other embodiments may place the R-peak elsewhere in the heartbeat window, for example, with a start time at 1779−(2×1500/5)=1179.

In various embodiments, identifying the sensed ECG trace segments by identifying common features and then identifying start and end times relative to the common features may facilitate identifying sensed ECG trace segments that generally include similar or repeated features, which may facilitate identification of outliers and/or the similar or repeated features.

Figure 7:
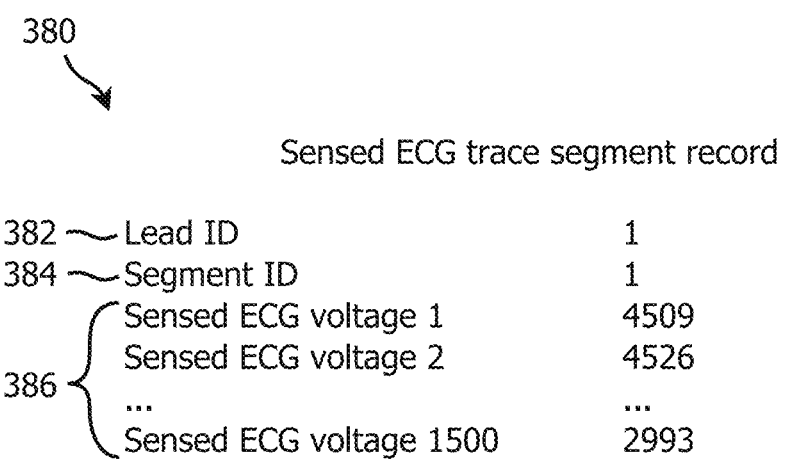
FIG. 7 is a representation of an exemplary sensed ECG trace segment record that may be used in the system shown in FIG. 1 in accordance with various embodiments.

Block 304 may direct the analyzer processor 100 to store a plurality of sensed ECG trace segment records generated according to the determined start and end points, in the location 144 of the storage memory 104. An exemplary sensed ECG trace segment record 380 that may be generated based on the value stored in the first R-peak identifier field 344 and stored in the location 142 of the storage memory 104, is shown in FIG. 7. The sensed ECG trace segment record 380 includes a lead identifier field 382 for storing a lead identifier identifying the lead, a segment identifier field 384 for storing a segment identifier identifying the segment, and sensed ECG voltage fields 386 storing values taken from the $1029^{th}$ to the $2529^{th}$ ECG voltage fields of the sensed ECG trace record 260 shown in FIG. 4.

Referring back to FIG. 3, block 208 directs the analyzer processor 100 to determine a representative ECG trace based on at least one of the identified corresponding sensed ECG trace segments. In some embodiments, block 208 may direct the analyzer processor 100 to identify a subset of the ECG trace segment records stored in the location 144 of the storage memory 104. In some embodiments, block 208 may direct the analyzer processor 100 to generate the representative ECG trace by averaging the ECG trace segment records included in the subset. In various embodiments, block 208 may direct the analyzer processor 100 to store the representative ECG trace in the location 146 of the storage memory 104.

Figure 8:
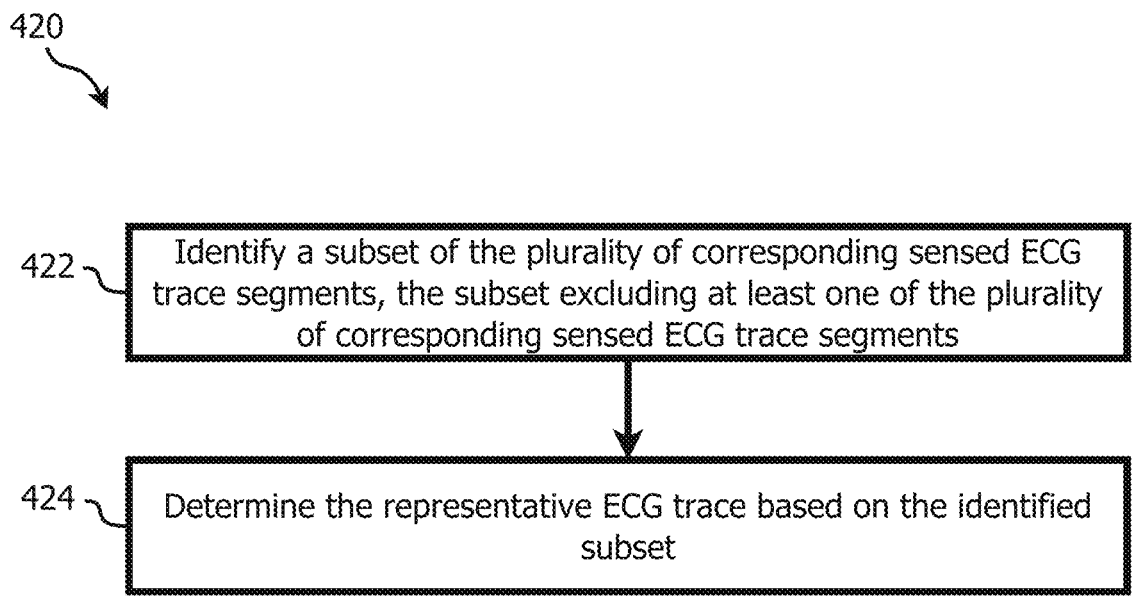
FIG. 8 is a flowchart depicting blocks of code that may be included in the blocks of code shown in FIG. 3 in accordance with various embodiments.

Referring to FIG. 8, there is shown a flowchart 420 depicting blocks of code that may be included in the block 208 in accordance with various embodiments. The flowchart 420 begins with block 422 which directs the analyzer processor 100 to identify a subset of the plurality of corresponding sensed ECG trace segments, the subset excluding at least one of the plurality of corresponding sensed ECG trace segments.

In various embodiments, by identifying a subset that excludes at least one of the plurality of corresponding sensed ECG trace segments, outliers may be removed from the data to be processed using the neural network classifier. In various embodiments, this may facilitate determining representative ECG traces without considering abnormal ECG trace segments and this may result in the representative ECG traces being better indicators of repeated features in the ECG trace segments. In various embodiments, this may facilitate faster and/or more accurate analysis by the ECG analyzer 12.

In some embodiments, block 422 may direct the analyzer processor 100 to use unsupervised multivariate classification such as principal component analysis (PCA) to decompose an ECG segment matrix defined by the ECG trace segment records for a particular lead and patient, stored in the location 144 of the storage memory 104 into a reduced dimensional space comprising an orthogonal basis in which each dimension represents a unique and independent contribution to the overall variance in the dataset. Block 422 may direct the analyzer processor 100 to then analyze the results of the multivariate classification to identify the at least one sensed ECG trace segment to be excluded from the subset.

Figure 9:
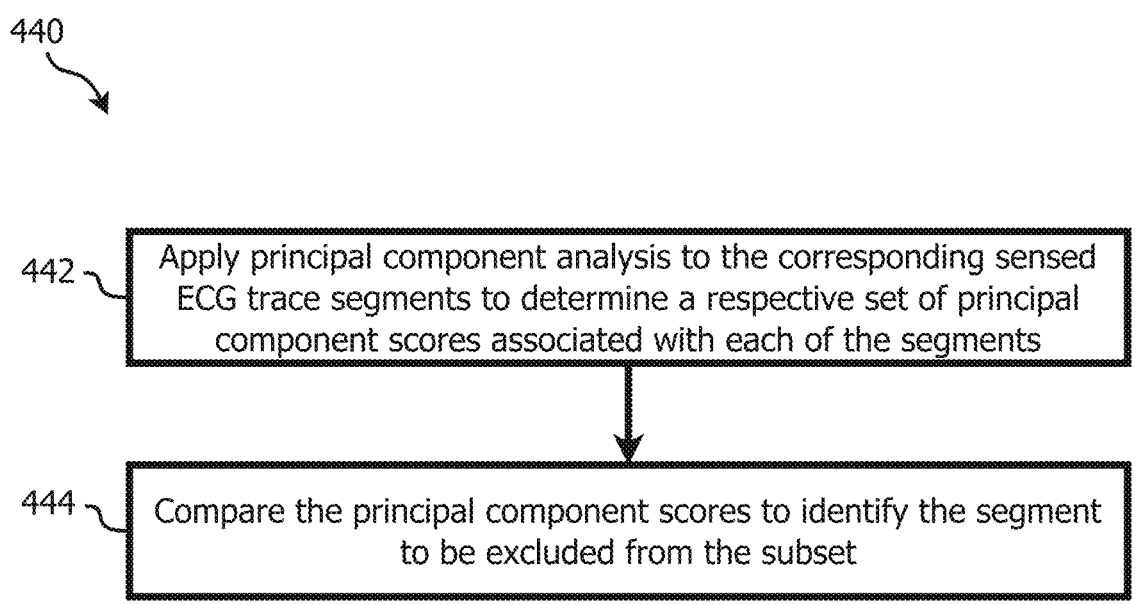
FIG. 9 is a flowchart depicting blocks of code that may be included in the blocks of code shown in FIG. 3 in accordance with various embodiments.

Referring to FIG. 9, there is provided a flowchart 440 depicting blocks of code that may be included in the block 422 of the flowchart 420 shown in FIG. 8, in various embodiments. The flowchart 440 begins with block 442 which directs the analyzer processor 100 to apply principal component analysis to the plurality of corresponding sensed ECG trace segments to determine a respective set of principal component scores associated with each of the corresponding sensed ECG trace segments. After block 442 has been executed, the ECG segment records for each patient-lead combination may be expressed in terms of principal component scores and loadings, based on this orthogonal basis.

In some embodiments, block 442 may direct the analyzer processor 100 to store the resulting principal component scores in the location 145 of the storage memory 104. In some embodiments, block 442 may direct the analyzer processor 100 to store 3 principal component scores in association with each of the ECG trace segments, in the location 145 of the storage memory 104. For example, in some embodiments, a 3-component principal component analysis may be applied to the ECG trace segments for each lead, producing scores and loadings for each of the ECG trace segments, representing the transformed data in an orthogonal basis. In some embodiments, execution of block 442 may be performed using software such as Python and the Python library, sklearn, for example. In some embodiments, the principal component scores may be stored as a matrix of float values in the location 145 of the storage memory 104.

Referring back to FIG. 9, block 444 directs the analyzer processor 100 to compare the principal component scores to identify the at least one of the plurality of corresponding sensed ECG trace segments to be excluded from the subset. In some embodiments, block 444 may direct the analyzer processor 100 to retrieve the principal component scores from the location 145 of the storage memory 104 and to calculate statistical measures of covariance for the principal component scores. In some embodiments block 444 may direct the analyzer processor 100 to calculate Hotelling's $T^2$ statistic, use PCA leveraging, and/or clustering calculations, for example.

In some embodiments, block 444 may direct the analyzer processor 100 to apply a confidence threshold to the principal component scores to identify those ECG segment records which represent ECG segments that are too dissimilar to the overall ECG segment matrix, e.g., in some embodiments, those segments whose distance from the center of the orthogonally-transformed ECG segment matrix is too great.

In some embodiments, for each principal component A, block 444 may direct the analyzer processor 100 to determine at least one confidence limit from the principal component scores and to, for each of the corresponding sensed ECG trace segments, compare the associated principal component score with the at least one confidence limit. In some embodiments, if the principal component score is outside of the at least one confidence limit, the associated trace segment may be identified as to be excluded from the subset.

For example, in some embodiments, block 444 may direct the analyzer processor 100 to determine a first and a second confidence limit, which may, in some embodiments be a 95% confidence limit, for example, by applying the Hotelling $T^2$ statistic, as follows:

$$\text{Conf.}(A)=\text{sqrt}[\sigma_{scores} \times \{A(N^2-1)/N(N-A)\} \times F_{critical}(0.05,N-A,A)]$$

where $F_{critical}$ represents the critical value of the F-distribution at 95% confidence, given the number of segmented traces N and the selected principal component A. In some embodiments, the confidence limit may be set at 95%, 99%, or another level. In some embodiments, block 444 may direct the analyzer processor 100 to determine a first confidence limit and a second confidence limit from the first and second principal component scores respectively, using the above equation. Block 444 may direct the analyzer processor 100 to, for each of the corresponding sensed ECG trace segments, compare the first and second principal component scores associated with the sensed ECG trace segment to the first and second confidence limits.

In some embodiments, the first two principal components may account for most of the variance, and the confidence limits of these principal components may serve well to define a confidence ellipse that has radii equal to these limits. In some embodiments, block 444 may direct the analyzer processor 100 to compare the scores from the N ECG trace segments with the confidence limits to determine which of the N ECG trace segments should be considered confidence outliers and excluded from the subset of ECG trace segments. For example, in some embodiments, block 444 may direct the analyzer processor 100 to plot the scores of the N ECG trace segments on the same axes as the ellipse and to distinguish points that fall within the ellipse, from confidence outlier points that do not. Accordingly, in some embodiments block 444 may direct the analyzer processor 100 to determine whether the first and second principal component scores are outside of an ellipse having a radius set by the first and second confidence limits, and if so, identify the sensed ECG trace segment to be excluded from the subset. In some embodiments, block 444 may direct the analyzer processor 100 to apply a Delaunay triangulation algorithm to distinguish the points that fall within the ellipse, from confidence outlier points that do not.

Figure 10:
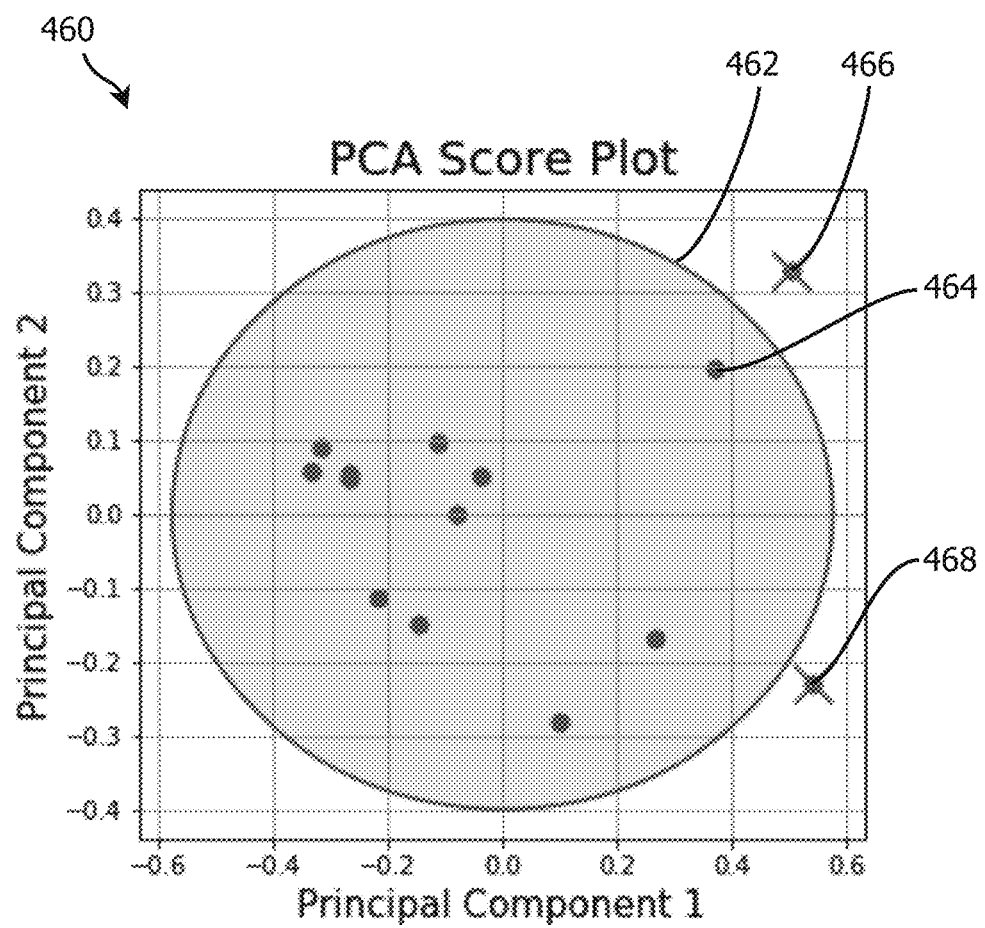
FIG. 10 is a representation of a plot showing a confidence ellipse that may be used in the system shown in FIG. 1 in accordance with various embodiments.

Referring to FIG. 10, there is provided a plot 460 showing a confidence ellipse 462 and points representing first and second principal component scores associated with respective ECG trace segments. In various embodiments, the ECG trace segments associated with principal component scores such as principal component scores 464 may be identified as within the ellipse defined by the first and second confidence limits. Principal component scores 466 and 468 may be identified as outside of the ellipse defined by the first and second confidence limits and therefore the ECG trace segments associated with the principal component scores 466 and 468 may be identified as confidence outliers to be excluded from the subset.

In some embodiments, more or fewer than 2 principal components may be used in applying the confidence limits. For example, in some embodiments, a single principal component may be used to define a single confidence limit which may be compared with a single principal component score for each ECG trace segment, to identify the outliers.

In some embodiments, block 444 may direct the analyzer processor 100 to compare the principal component scores in alternative or additional ways. For example, in some embodiments, block 444 may direct the analyzer processor 100 to calculate a PCA leverage for each of the ECG trace segments for a given lead based on the relationship of its score to all the scores, for example, according to:

$$\text{Lev.}(n)=N^{-1}+\Sigma_A[\text{score}(n,A)^2/\{\text{scores}(A)^T \times \text{scores}(A)\}]$$

In some embodiments, block 444 may direct the analyzer processor 100 to compare each leverage with the mean and standard deviation of all of the leverages for a given lead to determine whether the ECG trace segment associated with the leverage should be considered as a confidence outlier. For example, in some embodiments, block 444 may direct the analyzer processor 100 to determine whether the leverage of the ECG trace segment exceeds the mean plus twice the standard deviation of all leverages ($\mu+2\sigma$) and, if the leverage of a ECG trace segment exceeds the mean plus twice the standard deviation of all leverages ($\mu+2\sigma$), block 444 may direct the analyzer processor 100 to consider the ECG trace segment as a confidence outlier.

In some embodiments, block 444 may direct the analyzer processor 100 to apply a density-based spatial clustering of applications within noise (DBSCAN) algorithm to a scatter plot of the first two principal component scores. The DBSCAN algorithm may detect clusters within the plotted scores, using a previously set minimum number of traces that constitute a cluster and a previously set maximum distance between points, for example. In some embodiments, the minimum number of traces that constitute a cluster may be set to a value of 10, for example, and the maximum distance between points in a cluster may be to 0.5, for example. In various embodiments, block 444 may direct the analyzer processor 100 to consider any ECG trace segments associated with scores that are not within a cluster as confidence outliers. In some embodiments, this may facilitate rejection of small clusters, based on the assumption that ECG trace segments associated with small clusters represent sampling artifacts rather than average heartbeats.

In various embodiments, block 444 may direct the analyzer processor 100 to perform any or all of using a confidence limit, comparing leverages, and/or applying a DBSCAN algorithm to detect outliers, generally as described above, in order to identify ECG trace segments to be considered as confidence outliers.

In various embodiments, block 444 may direct the analyzer processor 100 to identify the subset of the plurality of corresponding sensed ECG trace segments by excluding the sensed ECG trace segments that are associated with or considered as confidence outliers.

In some embodiments, block 444 may direct the analyzer processor 100 to store copies of the ECG segment records that are not considered to be confidence outliers in the location 146 of the storage memory 104. In various embodiments, the ECG segment records stored in the location 146 of the storage memory 104 may act as a subset of the ECG segment records stored in the location 144 of the storage memory 104 and the subset may exclude at least one ECG segment record stored in the location 144.

Referring back to FIG. 8, block 424 then directs the analyzer processor 100 to determine the representative ECG trace based on the identified subset. In some embodiments, block 424 may direct the analyzer processor 100 to average the ECG segments represented by the ECG segment records stored in the location 146 of the storage memory 104. In some embodiments, other ways of determining the representative ECG trace may be used. For example, in some embodiments, block 424 may direct the analyzer processor 100 choose a median value for each of the 1,500 points in the heartbeat window.

In some embodiments, block 424 may direct the analyzer processor 100 to choose a single ECG segment or heartbeat to act as the representative ECG trace for analysis and classification. For example, in some embodiments, the ECG trace from which the ECG segments are derived may be a very short trace, including only a few complete heartbeats and, in these cases the statistical measures (PCA for example) may become less reliable due to a limited amount of data. In such cases, a single heartbeat may be selected arbitrarily as the representative ECG trace, for example based on the operator's judgment, though this may be avoided if at all possible. In some embodiments, a single ECG segment may be treated as the representative trace after being selected randomly from those deemed to not be outliers, i.e. those falling within the confidence regions as determined by the $T^2$ statistic, object leverage, the clustering, and/or another confidence test, if those values can be reliably calculated.

Figure 11:
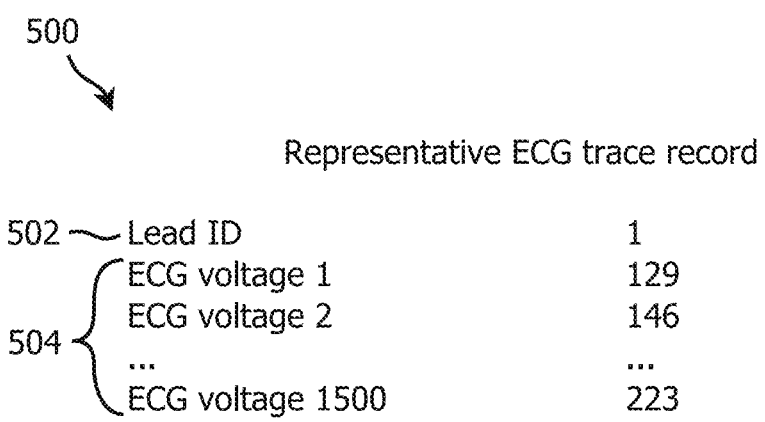
FIG. 11 is a representation of an exemplary representative ECG trace record that may be used in the system shown in FIG. 1 in accordance with various embodiments.

In various embodiments, block 424 may direct the analyzer processor 100 to store a representative ECG trace record as shown at 500 in FIG. 11 in the location 148 of the storage memory 104. Referring to FIG. 11, the representative ECG trace record 500 includes a lead identifier field 502 for storing a lead identifier identifying the lead from which the ECG trace was sensed and ECG voltage fields 504 for storing the average of values taken from the ECG segment records stored in the location 146 of the storage memory 104.

Referring back to FIG. 3, after the representative ECG trace record 500 is generated and stored in the location 148 of the storage memory 104, execution of block 208 may be completed.

Block 210 then directs the analyzer processor 100 to determine whether additional ECG traces need to be considered. In various embodiments, block 210 may direct the analyzer processor 100 to determine whether there are any additional sensed ECG trace records stored in the location 142 of the storage memory 104, which have not yet been considered as a subject sensed ECG trace at block 204 of the flowchart 200 shown in FIG. 3. If so, block 210 directs the analyzer processor 100 to return to block 204, which directs the analyzer processor 100 to consider one of the one or more sensed ECG traces as a subject sensed ECG trace. In various embodiments, block 204 may direct the analyzer processor 100 to consider a sensed ECG trace record from the location 142 of the storage memory 104 if the sensed ECG trace record has not yet been considered.

Blocks 206 and 208 may then be executed with respect to the newly considered sensed ECG trace record. In view of the foregoing, blocks 206 and 208 may be executed for each sensed ECG trace record stored in the location 142 of the storage memory 104.

Once all of the sensed ECG trace records have been considered, there may be a plurality of representative ECG trace records, each having generally the same format as the ECG trace record 500 shown in FIG. 11, stored in the location 148 of the storage memory 104. In various embodiments, there may be a respective representative ECG trace record for each of the sensed ECG trace records stored in the location 142 of the storage memory 104.

When all of the sensed ECG trace records have been considered, block 210 may direct the analyzer processor 100 to proceed to block 212.

Block 212 directs the analyzer processor 100 to cause at least one neural network classifier to be applied to the one or more determined representative ECG traces to determine one or more diagnostically relevant scores related to at least one diagnosis of the patient. In various embodiments, data defining a BrS diagnosis neural network classifier may be stored in the location 150 of the storage memory 104. In some embodiments, the BrS diagnosis neural network classifier may include a perceptron for BrS. In some embodiments, the data defining the BrS diagnosis neural network classifier may have been previously provided to the ECG analyzer 12. For example, in some embodiments, the data defining the BrS neural network classifier may have been determined during a training phase, which may have been performed by the ECG analyzer 12 and/or another device/system.

In some embodiments, block 212 may direct the analyzer processor 100 to concatenate the ECG voltage information included in the representative ECG trace records stored in the location 148 of the storage memory 104 and to use the concatenated data as an input for the BrS diagnosis neural network classifier. For example, in some embodiments, block 212 may direct the analyzer processor 100 to concatenate values from the ECG voltage fields of all of the representative training ECG trace records, in order from lead 1 to lead 12, for example, and to use that concatenated data as an input for the BrS diagnosis neural network classifier. In various embodiments, the order of leads for concatenation may need to match the order that was used in generating the neural network classifier. In some embodiments, block 212 may direct the analyzer processor 100 to cause patient data or factors of variation associated with the patient to also be used as an input for the BrS diagnosis neural network classifier.

In some embodiments, the patient data may include, for example, age, sex, and/or patient and/or family histories of arrhythmogenic cardiomyopathy-associated conditions and comorbidities. These may include, for example, numerical or Boolean representations of personal and/or family history of arrhythmogenic cardiomyopathy diagnoses including of BrS, family history of sudden cardiac death (SCD), personal history of syncope, and/or personal history of cardiac arrest. In some embodiments, for example, the patient data may include any or all of the following:

| Factor of Variation | Representation |
| --- | --- |
| Right Bundle Branch Block (RBBB) Class | Integer |
| Gender | Boolean (F/M - 0/1) |
| Age | Integer |
| Syncope | Boolean |
| Cardiac Arrest | Boolean |
| Family History of SD | Boolean |
| Family History of BrS | Boolean |

In various embodiments, the patient data may be stored in the location 152 of the storage memory 104. The patient data may have been previously provided by a medical professional, for example.

Figure 12:
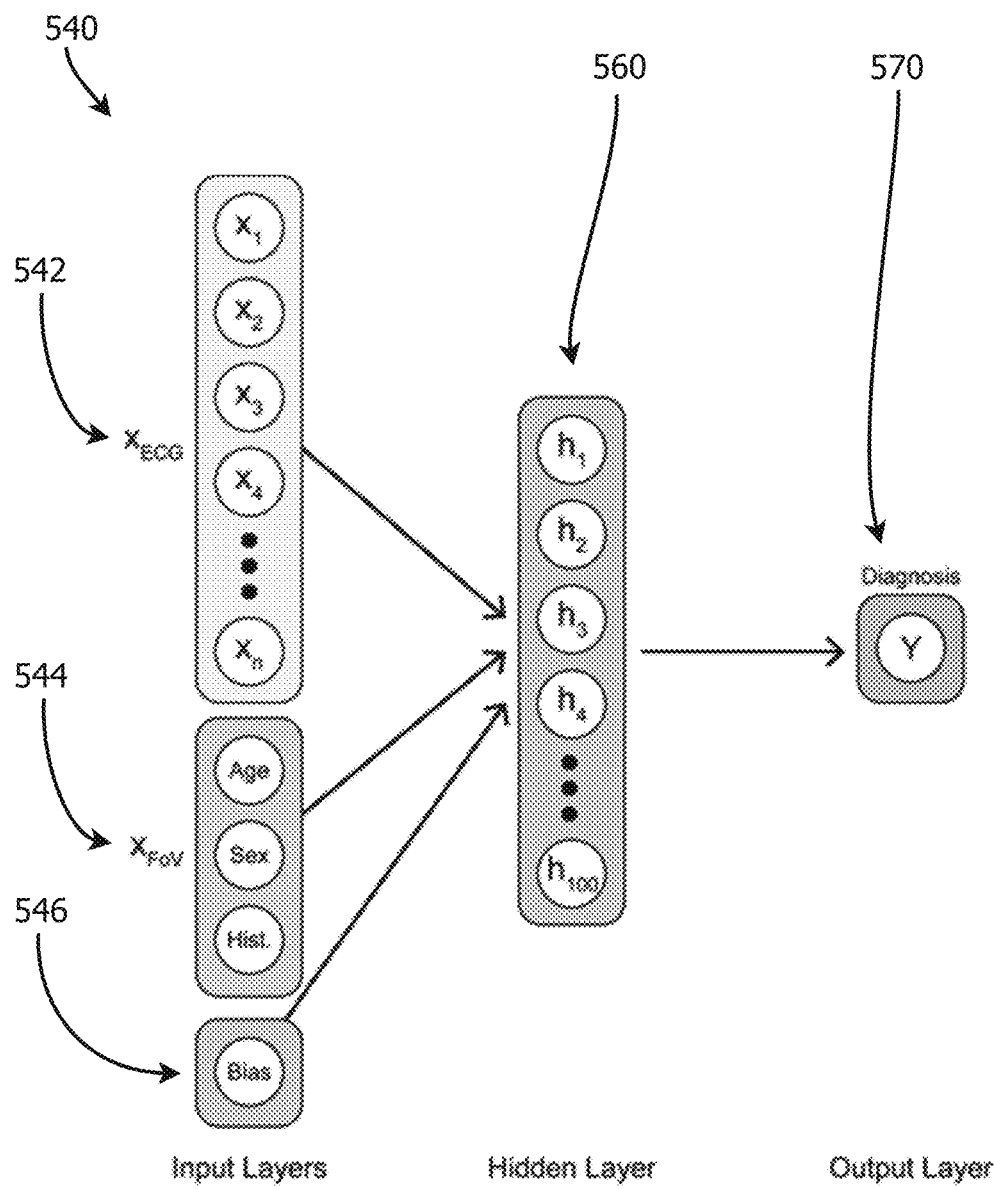
FIG. 12 is a representation of a BrS diagnosis neural network classifier that may be used in the system shown in FIG. 1 in accordance with various embodiments.

Referring to FIG. 12, there is shown a representation of the BrS diagnosis neural network classifier 540 that may be defined by data stored in the location 150 of the storage memory 104 in accordance with various embodiments. In some embodiments, the BrS diagnosis neural network classifier 540 may be configured to take $X_{ECG}$ inputs 542, which may include the concatenated representative ECG trace records, and $X_{FoV}$ inputs 544, which may include representations of the patient data associated with the patient. The input layer may also include a bias element 546.

In various embodiments, the BrS diagnosis neural network classifier 540 may include at least one hidden layer 560 containing neurons. For example, in some embodiments, there may be one hidden layer having 100 neurons. In some embodiments, additional and/or alternative hidden layers may be used.

In some embodiments, the BrS diagnosis neural network classifier 540 may include an output layer 570 including a classification representing positive (1) or negative (0) disease diagnosis. In various embodiments, the output layer 570 may provide a BrS diagnosis score which may represent a confidence in a diagnosis that the patient has BrS. In various embodiments, the BrS diagnosis score may be a decimal number between 0 and 1 with a very high score (close to 1) indicating a high confidence that the patient has the targeted disease or disorder and a very low score (close to 0) indicating a high confidence that the patient does not have BrS. In some embodiments, a BrS diagnosis score of greater than a threshold, such as, for example, 0.900, may be associated with a diagnosis of disease-positive. In some embodiments, a BrS diagnosis score of less than a threshold, such as, for example, 0.100, may be associated with a diagnosis of disease-negative.

In various embodiments, block 212 may direct the analyzer processor 100 to read the representative ECG trace records stored in the location 148, the patient data from the location 152 of the storage memory 104, and the definition of the BrS diagnosis neural network classifier from the location 150 and block 212 may direct the analyzer processor 100 to cause the BrS diagnosis neural network classifier to be applied to the concatenated ECG trace records, the patient data, and the bias element, which may have been defined in the definition of the BrS diagnosis neural network classifier, for example, to determine a BrS diagnosis score. In various embodiments, block 212 may direct the analyzer processor 100 to store a representation of the BrS diagnosis score in the location 154 of the storage memory 104.

In some embodiments, the flowchart 200 shown in FIG. 3 may include a further block for directing the analyzer processor 100 to produce signals representing the one or more diagnostically relevant scores for causing at least one display to display a representation of the one or more diagnostically relevant scores. For example, in some embodiments, the block may direct the analyzer processor 100 to transmit signals representing the BrS diagnosis score, taken from the location 154 of the storage memory 104, to the display 16 via the interface 122 of the I/O interface 112, for causing the display 16 to display the BrS diagnosis score as a binary or categorical indicator, and/or a number indicating probability of positive or negative diagnosis.

In various embodiments, the display 16 may be viewed by the patient and/or a medical professional and, upon viewing the representation of the BrS diagnosis score on the display 16, the patient and/or medical professional may take action. In various embodiments, upon viewing a high BrS diagnosis score indicating a high machine confidence that the patient has BrS, the patient may seek specialist medical advice to establish the most appropriate strategy to confirm diagnosis and to evaluate the risk of SCD according to the guidelines in the field.

In some embodiments, the block may include codes for directing the analyzer processor 100 to determine whether the BrS diagnosis score is greater than a disease-positive threshold score, such as, for example, 0.900, and if the BrS diagnosis score is greater than the threshold score, produce signals for causing the display 16 to present an indication that the patient is disease-positive.

In some embodiments, the block may include codes for directing the analyzer processor 100 to determine whether the BrS diagnosis score is less than a disease-negative threshold score, such as, for example, 0.100, and if the BrS diagnosis score is less than the threshold score, produce signals for causing the display 16 to present an indication that the patient is disease-negative.

Neural Network Training

Figure 13:
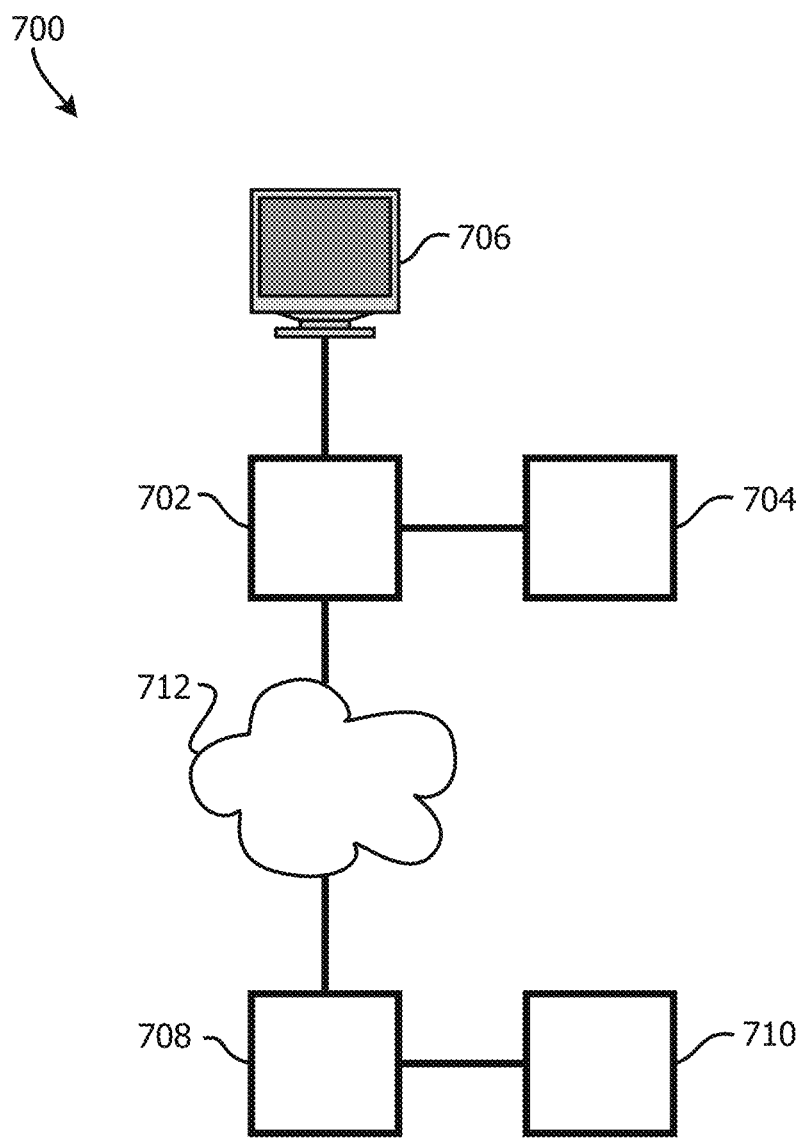
FIG. 13 is a schematic view of a system for facilitating for facilitating ECG analysis including neural network training according to various embodiments.

As discussed above, in various embodiments, neural network definition data may be stored in the location 150 of the storage memory 104 of the ECG analyzer 12. In some embodiments, the neural network definition data may have been generated during neural network training. Referring now to FIG. 13 there is shown a system 700 for facilitating ECG analysis including neural network training, in accordance with various embodiments.

Referring to FIG. 13, the system 700 includes an ECG analyzer 702 in communication with a patient ECG data source 704 and a display 706. In various embodiments, the ECG analyzer 702, the patient ECG data source 704, and the display 706 may include functionality generally similar to that described above having regard to the ECG analyzer 12, the ECG data source 14 and the display 16 shown in FIG. 1. In some embodiments, the ECG analyzer 702 may use as an input, an unknown patient electrocardiogram and use an ECG neural network classifier to predict a diagnosis of BrS and/or other primary electric disorders.

Referring to FIG. 13, in various embodiments, the system 700 also includes an ECG neural network trainer 708 in communication with an ECG training data source 710. In various embodiments, the ECG analyzer 702 may be in communication with the ECG neural network trainer 708 via a network 712, which may in some embodiments, include the Internet, for example.

In operation, the ECG neural network trainer 708 may be configured to use ECG data, including data taken from the ECG training data source 710 to train one or more neural network classifiers, such as, for example a BrS diagnosis neural network classifier. In some embodiments, the ECG neural network trainer 708 may be configured to use ECG data, including data taken from the ECG training data source 710 to train the BrS diagnosis neural network classifier described above with regard to the system 10 shown in FIG. 1, and to provide data defining the one or more neural network classifiers to the ECG analyzer 702 shown in FIG. 13. In some embodiments, the BrS neural network classifier may be trained from a complete data set of electrocardiograms accompanied by known medical diagnoses, represented in the diagnostic feature space as a binary categorical variable.

In some embodiments, in a training phase, the ECG neural network trainer 708 may collect ECG trace information from one or more patient ECG data sources, along with associated patient data and accompanying diagnoses, to build a curated data library stored in the ECG training data source 710. In some embodiments, as the data library grows in size, it may yield diagnostic models of increasing robustness and/or reliability.

Figure 14:
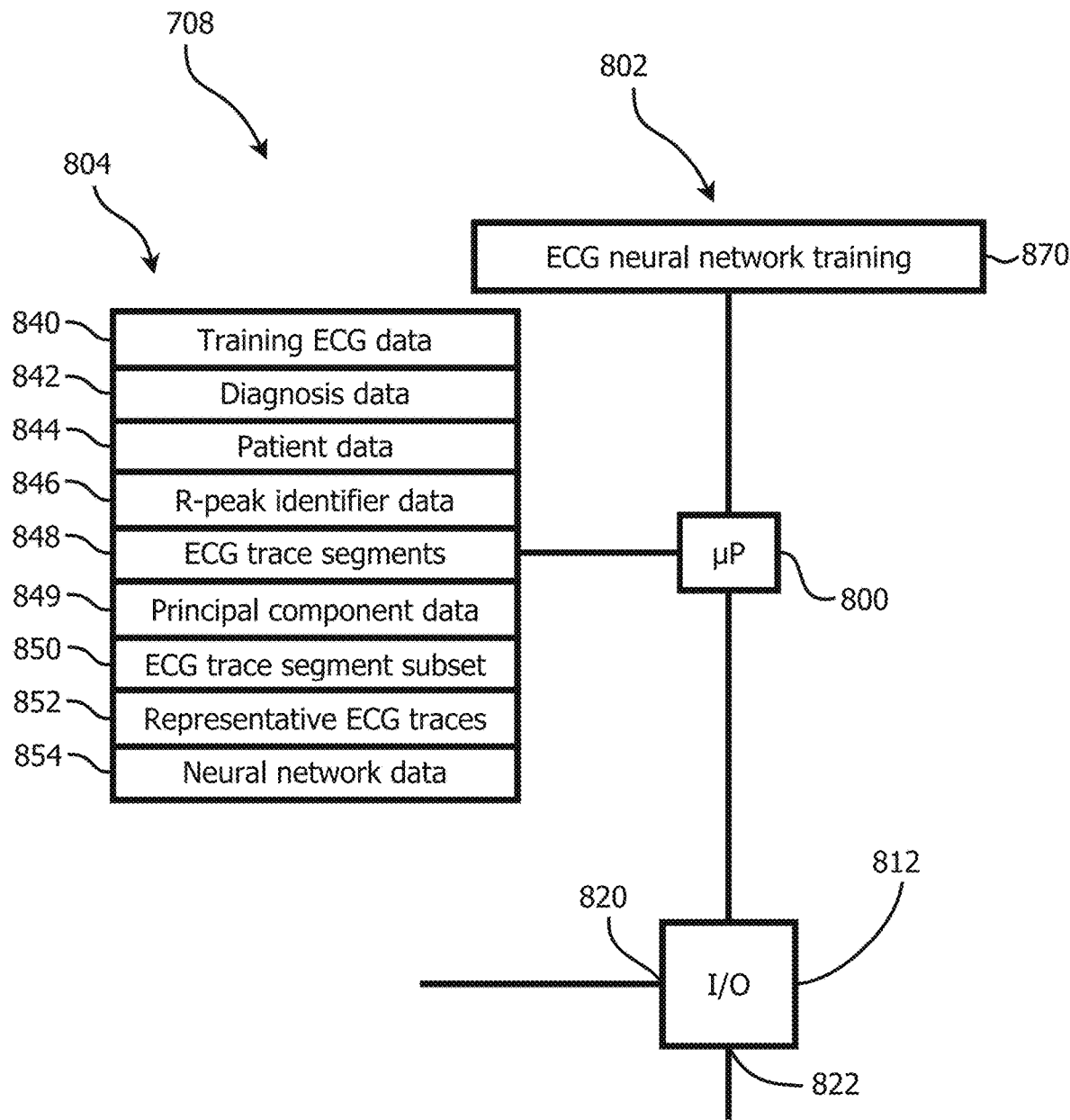
FIG. 14 is a schematic view of an ECG neural network trainer of the system shown in FIG. 13 including a processor circuit in accordance with various embodiments.

Referring to FIG. 14, a schematic view of the the ECG neural network trainer 708 of the system 700 shown in FIG. 13 according to various embodiments is shown. In various embodiments, elements of the ECG neural network trainer 708 that are similar to elements of the ECG analyzer 12 shown in FIG. 2 may function generally as described above having regard to the ECG analyzer 12 shown in FIG. 2.

Referring to FIG. 14, the ECG neural network trainer 708 includes a processor circuit including a trainer processor 800 and a program memory 802, a storage memory 804, and an input/output (I/O) interface 812, all of which are in communication with the trainer processor 800.

The I/O interface 812 includes an interface 820 for communicating with the ECG training data source 710 shown in FIG. 13 and an interface 822 for communicating with the ECG analyzer 702 via the network 712.

Processor-executable program codes for directing the trainer processor 800 to carry out various functions are stored in the program memory 802. Referring to FIG. 13, the program memory 802 includes a block of codes 870 for directing the ECG neural network trainer 708 to perform facilitating ECG neural network training functions.

The storage memory 804 includes a plurality of storage locations including location 840 for storing training ECG data, location 842 for storing diagnosis data, location 844 for storing patient data, location 849 for storing principal component data, location 846 for storing R-peak identifier data, location 848 for storing ECG trace segment data, location 850 for storing ECG trace segment subset data, location 852 for storing representative ECG trace data, and location 854 for storing neural network data.

In some embodiments, the program memory 802, the storage memory 804, and/or any portion thereof may be included in a device separate from the ECG neural network trainer 708 and in communication with the ECG neural network trainer 708 via the I/O interface 812, for example. In some embodiments, the functionality of the trainer processor 800 and/or the ECG neural network trainer 708 as described herein may be implemented using a plurality of processors and/or a plurality of devices, which may be distinct devices which are in communication via respective interfaces and/or a network, such as the Internet, for example.

Figure 15:
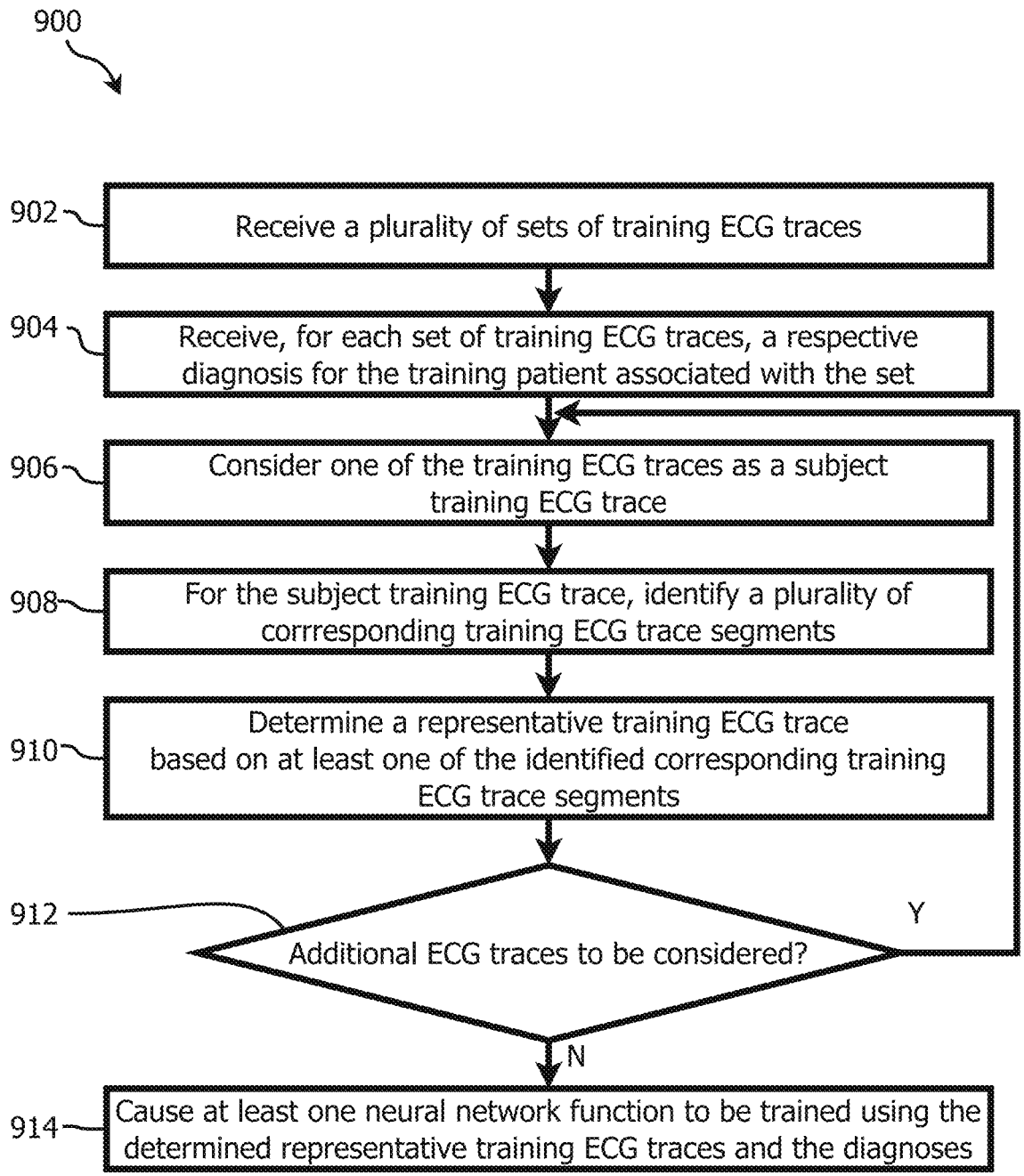
FIG. 15 is a flowchart depicting blocks of code for directing the ECG neural network trainer of the system shown in FIG. 13 to perform facilitating ECG neural network training functions in accordance with various embodiments.

In various embodiments, the ECG neural network trainer 708 shown in FIGS. 13 and 14 may be configured to facilitate ECG neural network training. Referring to FIG. 15, a flowchart depicting blocks of code for directing the trainer processor 800 shown in FIG. 14 to perform facilitating ECG neural network training functions in accordance with various embodiments is shown generally at 900. The blocks of code included in the flowchart 900 may be encoded in the block of codes 870 of the program memory 802 shown in FIG. 14, for example.

Referring to FIG. 15, the flowchart 900 begins with block 902 which directs the trainer processor 800 to receive a plurality of sets of training ECG traces, wherein each set of the sets of training ECG traces represents sensed heart activity over a training time period for a respective associated training patient of a plurality of training patients. Block 904 then directs the trainer processor 800 to receive, for each set of the plurality of sets of training ECG traces, a respective diagnosis for the training patient associated with the set of training ECG traces.

Figure 16:
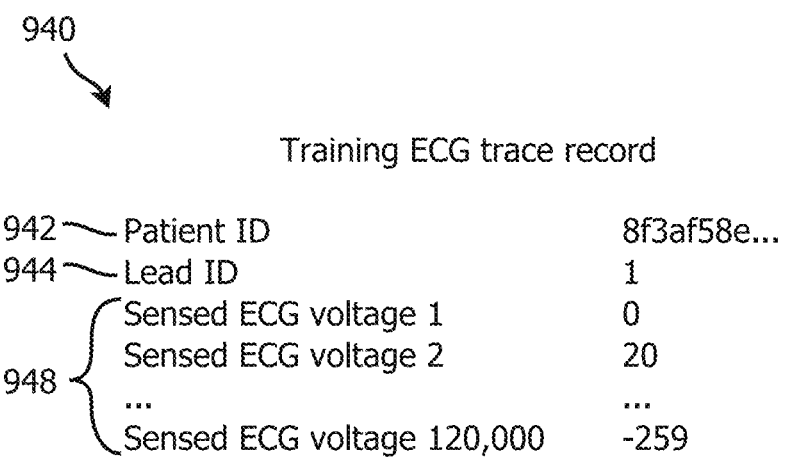
FIG. 16 is a representation of an exemplary training ECG trace record that may be used in the system shown in FIG. 13 in accordance with various embodiments.

In some embodiments, for example, the ECG training data source 710 may have previously been provided with training data including a set of training ECG traces and an associated diagnosis for each of a plurality of patients. In some embodiments, for example, the ECG training data source 710 may have stored thereon ECG training data for a plurality of training patients wherein the ECG data includes, for each patient, 12 training ECG trace records, an exemplary one of which is shown at 940 in FIG. 16, with each of the training ECG trace records representing a sensed ECG trace from one of 12 leads used with the patient. Referring to FIG. 16, the training ECG trace record 940 includes a patient identifier field 942 for storing a patient identifier identifying one of the training patients and a lead identifier field 944 for storing a lead identifier identifying the lead for which the training ECG trace record 940 was generated.

Referring still to FIG. 16, the training ECG trace record 940 also includes sensed ECG voltage fields 948 which may be generally as described above having regard to the ECG trace record 260 shown in FIG. 4. In various embodiments, the 12 training ECG trace records stored by the ECG training data source 710 for a training patient may act as a set of training ECG traces representing sensed heart activity over a training time period for the training patient.

In some embodiments, the ECG training data stored by the ECG training data source 710 may include a respective diagnosis for each of the training patients and therefore for each of the sets of training ECG traces. In various embodiments, for example, the ECG training data may include a plurality of diagnosis records, an exemplary one of which is shown at 1000 in FIG. 17, each of the diagnosis records associated with a training patient and a set of training ECG trace records. In some embodiments, the diagnosis record 1000 may be associated with a training patient and a set of training ECG traces by including a patient identifier field 1002 for storing a patient identifier that may be common with the patient identifier included in the set of training ECG traces.

Figure 17:
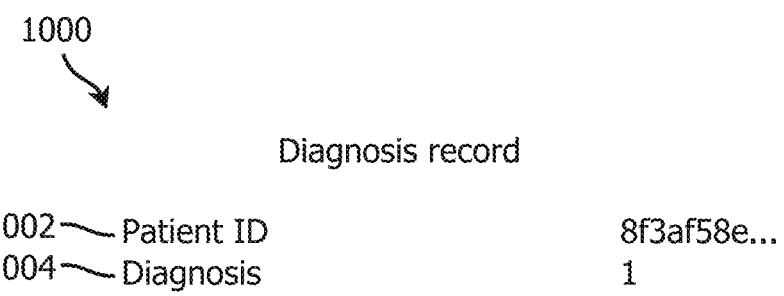
FIG. 17 is a representation of an exemplary diagnosis record that may be used in the system shown in FIG. 13 in accordance with various embodiments.

Referring to FIG. 17, the diagnosis record 1000 may also include a diagnosis field 1004 for storing a diagnosis identifier representing a diagnosis for the training patient identified by the patient identifier stored in the patient identifier field 1002. For example, in some embodiments, the diagnosis field 1004 may store a BrS diagnosis identifier value which may be set to 1 if the patient is diagnosed with BrS and may be set to 0 if the patient is diagnosed as not having BrS.

In some embodiments, the values for the diagnosis identifier fields in the diagnosis records stored in the ECG training data source 710 may have been previously provided by medical professionals, who may have reviewed the associated set of training ECG traces and/or other patient related information.

Referring back to FIG. 15, block 902 may direct the trainer processor 800 to receive a message including a representation of the training ECG trace records stored in the ECG training data source 710 via the interface 820, for example. In some embodiments, block 902 may direct the trainer processor 800 to store the training ECG trace records in the location 840 of the storage memory 804 shown in FIG. 14.

Block 904 may direct the trainer processor 800 to receive a message including a representation of the diagnosis records stored in the ECG training data source 710 via the interface 820, for example. In some embodiments, block 904 may direct the trainer processor 800 to store the diagnosis records in the location 842 of the storage memory 804 shown in FIG. 14.

In some embodiments, blocks 902 and 904 may be executed concurrently and the sets of training ECG traces and associated diagnoses may be received contemporaneously.

In some embodiments, the ECG training data source 710 may have stored thereon patient data or factors of variation associated with each of the training patients and the flowchart 900 may include a block of codes directing the trainer processor 800 to receive representations of the patient data. In some embodiments, for example, the patient data may have been stored in a plurality of patient data records in the ECG training data source 710 and each may include a patient identifier field and one or more patient data fields storing one or more patient data values representing patient data for the training patient identified by the patient identifier field. In such embodiments, the flowchart 900 may include blocks of code directing the trainer processor 800 to receive representations of the patient data records from the ECG training data source 710 via the interface 820, for example. In some embodiments, the block may direct the trainer processor 800 to store the patient data in the location 844 of storage memory 804.

In view of the foregoing, after execution of blocks 902 and 904, the ECG neural network trainer 708 may have stored in the locations 840 and 842 of the storage memory 804 a plurality of sets of training ECG trace records and a respective diagnosis record associated with each of the sets of training ECG trace records. In some embodiments, the ECG neural network trainer 708 may also have stored in the location 844 of the storage memory 804 additional patient data. In various embodiments, this information may act as training ECG data which may be used to train at least one neural network classifier, as described below.

Referring to FIG. 15, blocks 906 to 912 of the flowchart 900 shown in FIG. 15 may function generally similarly to blocks 204 to 210 of the flowchart 200 shown in FIG. 3, except that blocks 906 to 912 may be executed with respect to each training ECG trace record stored in the location 840 of the storage memory 804.

Block 906 directs the trainer processor 800 to consider one of the training ECG traces as a subject training ECG trace. In some embodiments, upon a first execution of block 906, block 906 may direct the trainer processor 800 to consider a first training patient identifier and to consider a first training ECG trace record having a patient identifier that matches the first training patient identifier. In some embodiments, for example, block 906 may direct the trainer processor 800 to consider the training ECG trace record 940 shown in FIG. 16 as the first training ECG trace record.

Block 908 then directs the trainer processor 800 to, for the subject training ECG trace, identify a plurality of corresponding training ECG trace segments, each of the training ECG trace segments representing patient heart activity over a segment of the training time period. In some embodiments, block 908 may include code generally similar to that included in block 206 of the flowchart 200 shown in FIG. 3 and discussed above.

In various embodiments, after execution of block 908 shown in FIG. 15, a training R-peak identifier record having format generally similar to the R-peak identifier record 340 shown in FIG. 6, except that the training R-peak identifier may include a patient identifier field, may be stored in the location 846 of the storage memory 804 and a plurality of training ECG trace segment records, each having format generally similar to the sensed ECG trace segment record 380 shown in FIG. 7, except that the training ECG trace segment records each have a patient identifier field, may be stored in the location 848 of the storage memory 804.

Block 910 then directs the trainer processor 800 to determine a representative training ECG trace based on at least one of the identified corresponding training ECG trace segments. In various embodiments, block 910 may include code generally similar to that of block 210 of the flowchart 200 shown in FIG. 3 and discussed above.

Figure 18:
FIG. 18 is a representation of an exemplary representative training ECG trace record that may be used in the system shown in FIG. 13 in accordance with various embodiments.

In some embodiments, block 910 may direct the trainer processor 800 to identify or determine a subset of the training ECG trace segment records determined at block 908. In some embodiments, block 910 may direct the trainer processor 800 to store principal component data in the location 149 of the storage memory 804. In various embodiments, block 910 may direct the trainer processor 800 to store the identified training ECG trace segment records in the location 850 of the storage memory 804. In some embodiments, block 910 may direct the trainer processor 800 to determine a representative training ECG trace record based on the training ECG trace segment records stored in the location 850 of the storage memory 804, the representative training ECG trace record having generally the same format as the representative ECG trace record 500 shown in FIG. 11, except that the representative training ECG trace record may include a patient identifier field. In some embodiments, block 910 may direct the trainer processor 800 to store the representative training ECG trace record in the location 852 of the storage memory 804. Referring to FIG. 18, there is shown an exemplary representative training ECG trace record 1040 that may be stored in the location 852 of the storage memory 804 in various embodiments.

Block 912 then directs the trainer processor 800 to determine whether there are any additional training ECG traces to be considered. In some embodiments, block 912 may direct the trainer processor 800 to determine whether any training ECG trace records stored in the location 840 of the storage memory 804 have not yet been considered as a subject training ECG trace for the purposes of blocks 908 and 910 of the flowchart 900 shown in FIG. 15. If additional training ECG traces are to be considered, the trainer processor 800 returns to block 906 and a further training ECG trace record is considered. If all of the training ECG trace records stored in the location 840 of the storage memory 804 have been considered, the trainer processor 800 proceeds to block 914.

Accordingly, when the trainer processor 800 proceeds to block 914, there may be stored in the location 848 of the storage memory 804, a plurality of sets of representative training ECG trace records, each representative training ECG trace record including a patient identifier field identifying a training patient for which the record was determined and a lead identifier field identifying the lead for which the record was determined. In some embodiments, the location 848 of the storage memory 804 may store representative training ECG trace records for a few hundred patients, which may provide acceptable accuracy for disease identification, such as, for example, accuracy approaching about 70% in some embodiments. In some embodiments, the location 848 of the storage memory 804 may store representative training ECG trace records for over 1000 patients, which may provide accuracy of about 85% in some embodiments. In some embodiments, the location 848 of the storage memory 804 may store representative training ECG trace records for over 10,000 patients or over 100,000 patients.

Block 914 directs the trainer processor 800 to cause at least one neural network classifier to be trained using the representative training ECG traces and the diagnoses. In some embodiments, initial neural network data defining the architecture of a BrS diagnosis neural network classifier and/or an initial BrS diagnosis neural network classifier itself may be stored in the location 854 of the storage memory 804. In various embodiments, the initial neural network data may have been previously provided when setting up the ECG neural network trainer 708, for example.

In some embodiments, the architecture of the BrS diagnosis neural network classifier may include a multilayer perceptron based on a feed-forward artificial neural network, consisting of input, hidden, and output layers. For example, the general architecture for the BrS diagnosis neural network classifier may be represented as shown at 540 in FIG. 12. Hidden layers included in this neural network classifier may map the input layer to a binary categorical output layer (which may include a representation of a diagnosis, for example a BrS diagnosis value). In some embodiments, a hidden layer containing 100 neurons may be used, though in some embodiments more or fewer neurons and/or layers may be used. In some embodiments, block 914 may direct the trainer processor 800 to use the data from the ECG voltage fields of the representative training ECG trace records stored in the location 852 of the storage memory 804 and the patient data stored in the location 844 of the storage memory 804 as inputs and the diagnosis field values of the diagnosis records stored in the location 842 of the storage memory 804 as respective desired outputs, for each training patient, to train the BrS diagnosis neural network classifier and update the data defining the BrS diagnosis neural network classifier stored in the location 854 of the storage memory 804.

For example, in some embodiments, block 914 may direct the trainer processor 800 to, for a particular patient or patient identifier, concatenate the values from the ECG voltage fields of all of the representative training ECG trace records for the patient, in order from lead 1 to lead 12, for example, and to use that as $X_{ECG}$ inputs 542 and to use the values from the patient data fields for that patient stored in the location 844 of the storage memory 804 as $X_{FoV}$ inputs 544 and to use the value from the diagnosis field for the patient as a desired output.

In some embodiments, block 914 may direct the trainer processor 800 to train the hidden layers to map the input layer to the binary categorical output layer using an optimization algorithm, such as, for example, scaled conjugate gradient descent, stochastic gradient descent, adaptive moment estimation, and/or any other optimization algorithm, coupled with a backpropagation algorithm, such that the neural network classifier is trained using data for a plurality of the training patients.

In some embodiments, block 914 may direct the trainer processor 800 to produce associated quantitative performance data that characterizes the accuracy of the classifications, such as, for example, by benchmarking the neural network by means of a confusion matrix or an area-under-the-curve receiver-operator characteristic (AUC-ROC). In some embodiments, block 914 may direct the trainer processor 800 to employ an optimization algorithm that minimizes one such performance measure, for example a logarithmic loss function, otherwise termed a binary cross-entropy function, which quantifies the probability of incorrect classification in the logarithmic numerical space. In various embodiments, a particular neural network training method (i.e., splitting the data randomly into parts, rejecting certain training data based on the results, and retraining) may be chosen when building the neural network classification model.

In various embodiments, after block 914 has been executed, data defining a trained BrS diagnosis neural network classifier may be stored in the location 854 of the storage memory 804.

In some embodiments, block 914 may direct the trainer processor 800 to produce signals representing the trained BrS diagnosis neural network classifier for causing a representation of the trained BrS diagnosis neural network classifier to be transmitted to the ECG analyzer 702 shown in FIG. 13. In some embodiments, the ECG analyzer 702 may include a processor circuit generally as shown in FIG. 2 and the ECG analyzer 702 may direct the analyzer processor of the ECG analyzer 702 to store the representation of the trained BrS diagnosis neural network classifier in a location similar to the location 150 of the ECG analyzer 12 shown in FIG. 2.

In various embodiments, the ECG analyzer 702 may be configured to execute the flowchart 200 shown in FIG. 3, generally as described above, to use the trained BrS diagnosis neural network classifier and determine a BrS diagnosis score for a patient.

Various Embodiments

In some embodiments, any or all of the system 10 shown in FIG. 1 may be implemented as a single device or as separate devices. For example, in some embodiments, functionality described herein as performed by the ECG analyzer 12 may be performed by separate devices. For example, in some embodiments, the ECG analyzer 12, ECG data source 14, and the display 16 may be incorporated into a single device, which may be a wearable device, such as a fitness tracker and/or wrist watch device, for example, which may be configured to capture ECG data using sensors included in the device.

In some embodiments, a portable embodiment of the ECG data source 14 may collect an ECG trace record 260 during a longer time period of measurement, such as overnight or over a period of one or more days, for example, in order to capture rare or isolated heartbeat intervals of diagnostic utility.

In some embodiments, the ECG analyzer 12 may be implemented using more than one device and/or processor circuit, such that various functionalities of the ECG analyzer 12 may be performed by different devices.

In some embodiments, the application of the at least one neural network classifier may be performed by a neural network processing device in communication with the ECG analyzer 12, for example, to reduce processing requirements of the ECG analyzer 12. In such embodiments, the data defining the at least one neural network classifier may be stored on the neural network processing device, and block 212 of the flowchart 200 shown in FIG. 3 may direct the ECG analyzer 12 to transmit the inputs for at least one neural network to the neural network processing device to cause the device to determine the one or more diagnostically relevant scores. In some embodiments, the neural network processing device may be configured to send a representation of the one or more diagnostically relevant scores to the ECG analyzer 12, once they are determined.

In various embodiments, additional or fewer leads may be used to generate the sensed ECG trace records. For example, in some embodiments, a single sensed ECG trace record may be generated and the ECG analyzer 12 may be configured to use the single sensed ECG trace record. Accordingly, in various embodiments, blocks 204 and 210 of the flowchart 200 shown in FIG. 3 may be omitted.

In some embodiments, data handled by the ECG analyzer 12 may be associated with a particular patient. For example, in some embodiments, the sensed ECG trace record 260, R-peak identifier record 340, sensed ECG trace segment record 380, and representative ECG trace record 500 may all include patient identifier fields for storing a patient identifier identifying the patient to which the data applies.

In some embodiments, the ECG neural network trainer 708 of the system 700 shown in FIG. 13 may be configured to update the neural network data stored in the location 854 of the storage memory 804 shown in FIG. 14. For example, in some embodiments, the ECG neural network trainer 708 may be configured to receive a set of training ECG traces and an associated diagnosis for a new training patient and to update the neural network data using the received information. In some embodiments, once the neural network data has bene updated, the ECG neural network trainer 708 may transmit to the ECG analyzer 702 the updated neural network information.

In some embodiments, the system 700 may include a plurality of systems generally similar to the system 10 shown in FIG. 1, each in communication with the ECG neural network trainer 708, and the ECG neural network trainer may be configured to send the updated neural network information to each of the ECG analyzers included in the systems.

While in some embodiments described above, the systems 10 and/or 700 shown in FIGS. 1 and 13 may be configured to facilitate diagnosis of BrS in particular, in various embodiments, additional or alternative syndromes, diseases, and/or disorders may be diagnosed or aided in the diagnosing using a system generally similar to the systems 10 and/or 700 described above, such as analytic, possibly idiopathic primary electric disorders such as for example Wolff-Parkinson-White Syndrome, early repolarization syndrome, long-QT syndrome, short-QT syndrome, and complete or incomplete right or left branch bundle block, as well as cardiomyopathies, such as, for example arrhythmogenic right ventricular cardiomyopathy or dysplasia, left ventricular non-compaction, hypertrophic cardiomyopathy, dilated cardiomyopathy, ischemic cardiomyopathy, restrictive cardiomyopathy, and/or other idiopathic cardiomyopathies.

Accordingly, in various embodiments, the BrS diagnosis neural network classifier described herein may be replaced by another arrhythmogenic disease diagnostic neural network classifier configured to output a diagnosis score for an arrhythmogenic disease diagnosis. In such embodiments, the arrhythmogenic disease diagnostic neural network classifier may be trained using data associated with the arrhythmogenic disease diagnosis.

Referring to FIGS. 19-24, there are shown respective representations of baseline ECGs 1100, 1120, 1140, 1160, 1180, and 1200 that capture resting states of respective patients, together with respective representations of ECGs 1102, 1122, 1142, 1162, 1182, and 1202 obtained after challenging the respective patients by administration of the sodium-channel blocking drug, ajmaline.

Figure 19:
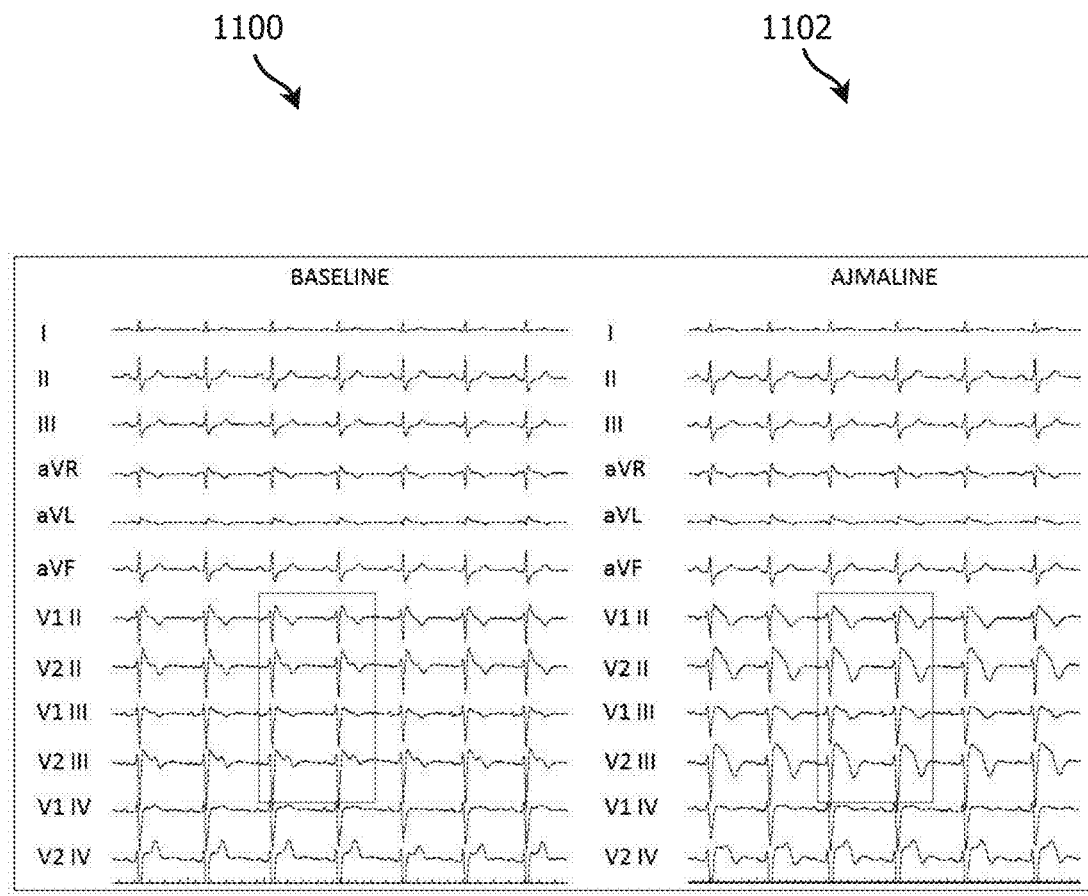
FIG. 19 is a representation of a baseline ECG for a patient and an ECG obtained after challenging the patient in accordance with various embodiments.

Referring to FIG. 19, the patient exhibits a type 2 BrS pattern, which changes to type 1 after administration of ajmaline. In some embodiments, the ECG analyzer 12 of the system 10 shown in FIG. 1 may correctly identify the disease state of this patient as disease-positive from an analysis of the baseline ECG 1100. In some embodiments, for example, the BrS score determined based on the baseline ECG 1100 may be 0.998.

Figure 20:
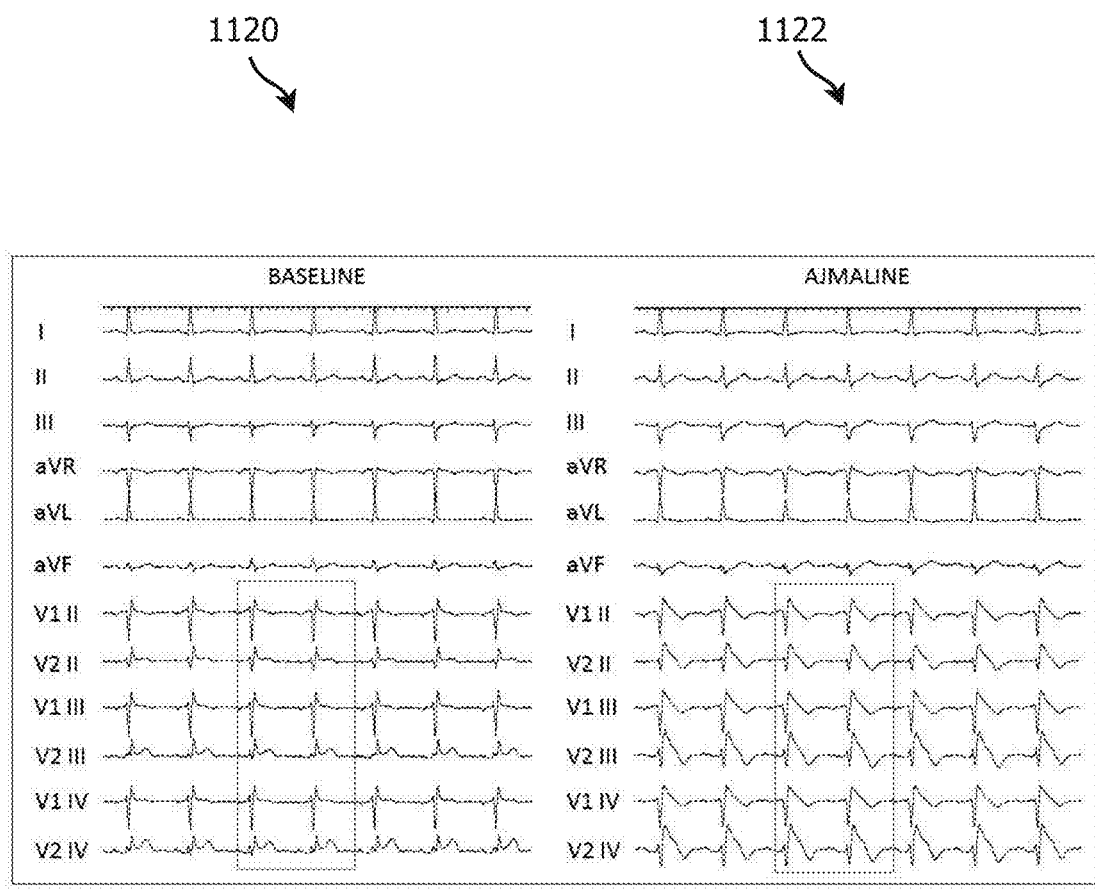
FIG. 20 is a representation of a baseline ECG for a patient and an ECG obtained after challenging the patient in accordance with various embodiments.

Referring to FIG. 20, the baseline ECG 1120 shows incomplete right bundle branch block turning into type 1 BrS ECG pattern after ajmaline challenge. In some embodiments, the ECG analyzer 12 of the system 10 shown in FIG. 1 may correctly identify the disease state of this patient as disease-positive from an analysis of the baseline ECG 1120. In some embodiments, for example, the BrS score determined based on the baseline ECG 1120 may be 1.000.

Figure 21:
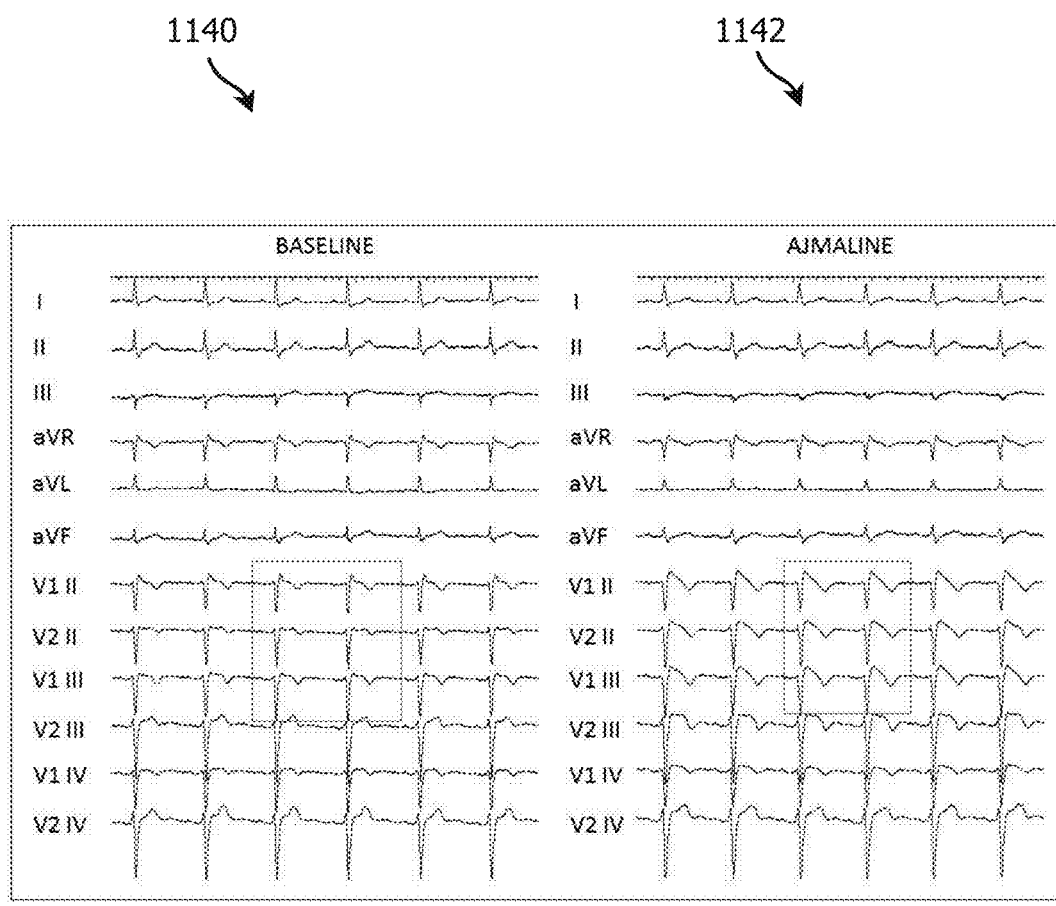
FIG. 21 is a representation of a baseline ECG for a patient and an ECG obtained after challenging the patient in accordance with various embodiments.

Referring to FIG. 21, the baseline ECG 1140 shows mild abnormalities in the high right precordial leads with ajmaline challenge resulting positive for Brs showing type 1 pattern. In some embodiments, the ECG analyzer 12 of the system 10 shown in FIG. 1 may correctly identify the disease state of this patient as disease-positive from an analysis of the baseline ECG 1140. In some embodiments, for example, the BrS score determined based on the baseline ECG 1140 may be 1.000.

Figure 22:
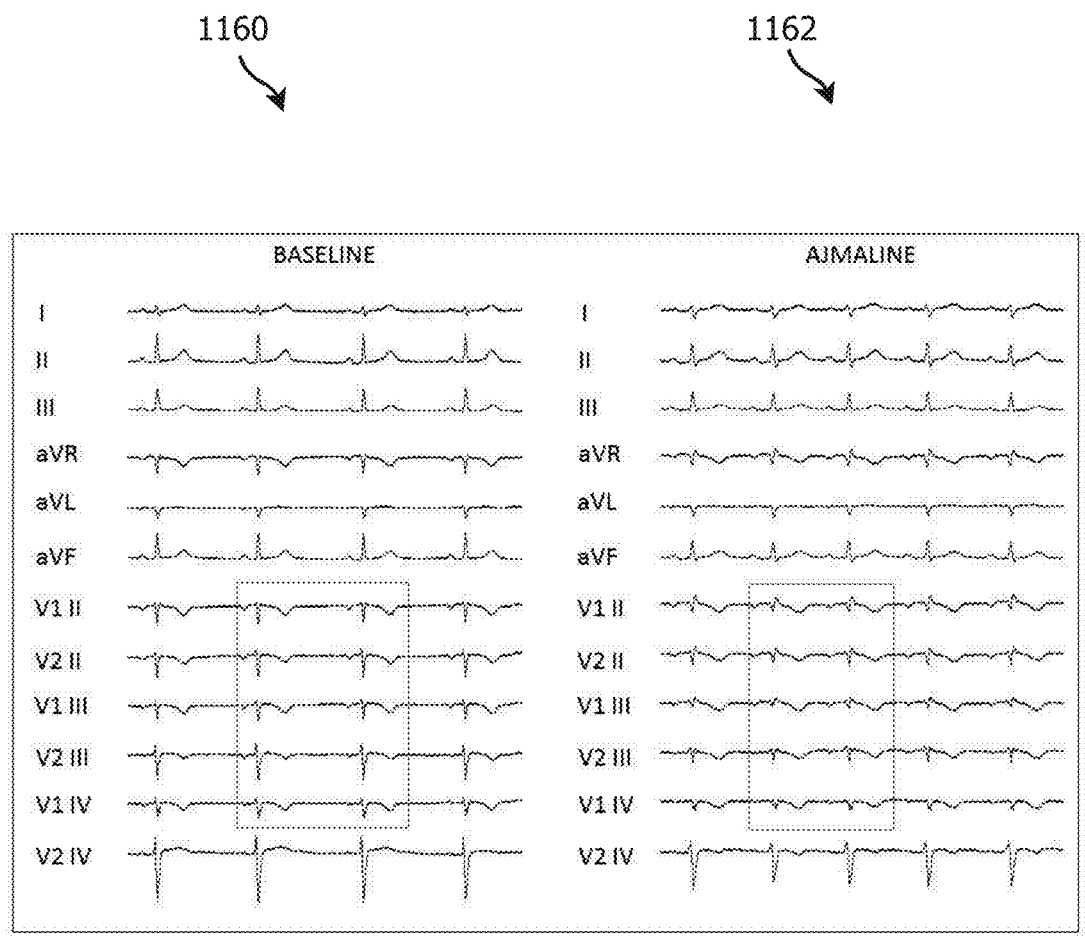
FIG. 22 is a representation of a baseline ECG for a patient and an ECG obtained after challenging the patient in accordance with various embodiments.

Referring to FIG. 22, analysis of the baseline ECG 1160 and ECG 1162 after ajmaline challenge may be consistent with a negative diagnosis of BrS. In some embodiments, the ECG analyzer 12 of the system 10 shown in FIG. 1 may correctly identify the disease state of this patient as disease-negative from an analysis of the baseline ECG 1160. In some embodiments, for example, the BrS score determined based on the baseline ECG 1160 may be 0.058. In some embodiments, a confidence of the negative diagnosis may be determined as the BrS score subtracted from 1 (e.g., 1−0.058=0.942).

Figure 23:
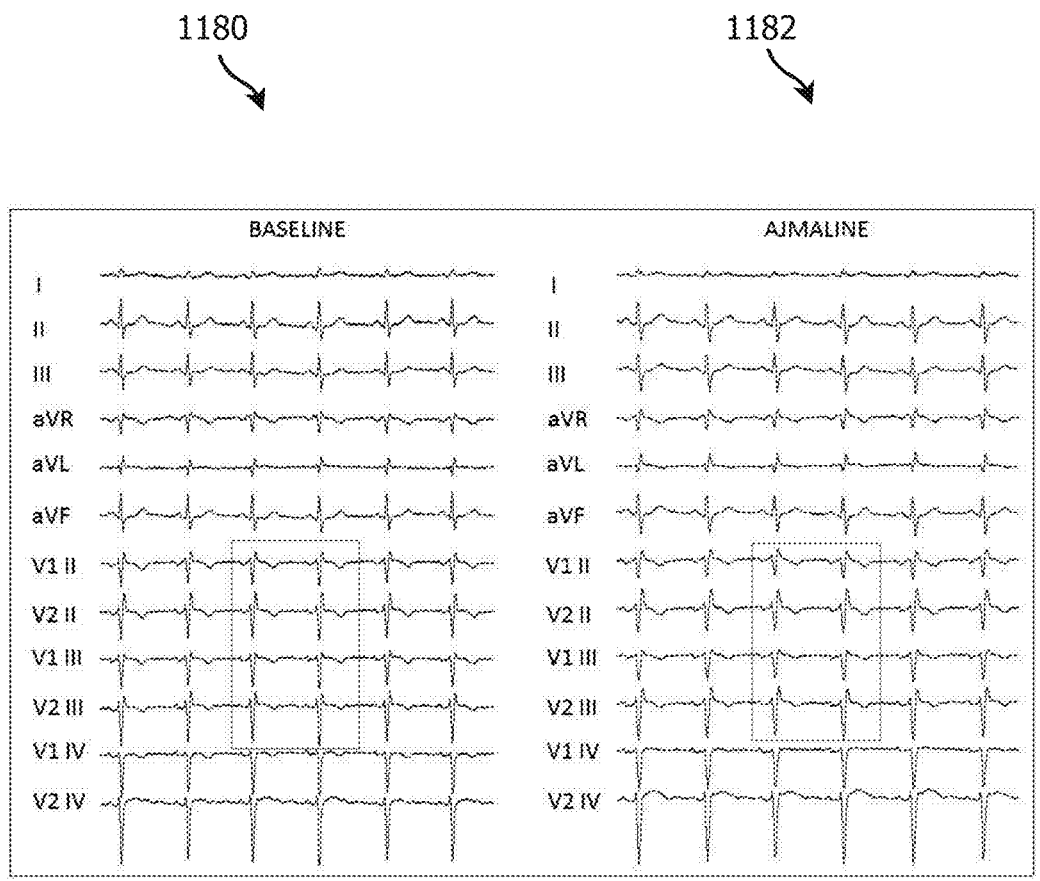
FIG. 23 is a representation of a baseline ECG for a patient and an ECG obtained after challenging the patient in accordance with various embodiments.

Referring to FIG. 23, analysis of the baseline ECG 1180 and ECG 1182 after ajmaline challenge may be consistent with a negative diagnosis of BrS. In some embodiments, the ECG analyzer 12 of the system 10 shown in FIG. 1 may correctly identify the disease state of this patient as disease-negative from an analysis of the baseline ECG 1180. In some embodiments, for example, the BrS score determined based on the baseline ECG 1180 may be 0.028.

Figure 24:
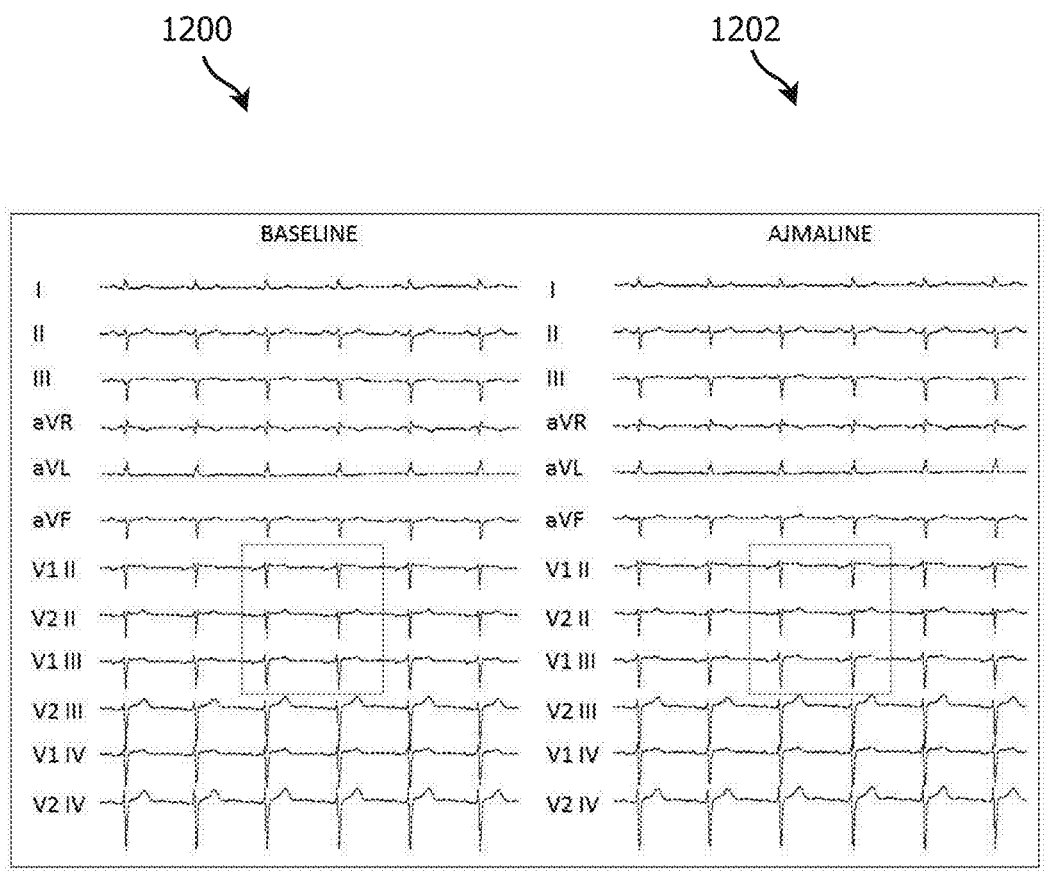
FIG. 24 is a representation of a baseline ECG for a patient and an ECG obtained after challenging the patient in accordance with various embodiments.

Referring to FIG. 24, analysis of the baseline ECG 1200 and ECG 1202 after ajmaline challenge may be consistent with a negative diagnosis of BrS. In some embodiments, the ECG analyzer 12 of the system 10 shown in FIG. 1 may correctly identify the disease state of this patient as disease-negative from an analysis of the baseline ECG 1200. In some embodiments, for example, the BrS score determined based on the baseline ECG 1200 may be 0.010.

While specific embodiments of the invention have been described and illustrated, such embodiments should be considered illustrative of the invention only and not as limiting the invention as construed in accordance with the accompanying claims.

What is claimed is:

1. A computer-implemented method of facilitating electrocardiogram ("ECG") analysis, the method comprising:
   receiving one or more sensed ECG traces for a patient, each of the sensed ECG traces representing sensed patient heart activity over a sensed time period;
   for each of the one or more sensed ECG traces:
      identifying a plurality of corresponding sensed ECG trace segments, each of the sensed ECG trace segments representing sensed patient heart activity for the patient over a segment of the sensed time period; and
      determining a representative ECG trace based on at least one of the identified corresponding sensed ECG trace segments; and
   causing at least one neural network classifier to be applied to the one or more determined representative ECG traces to determine one or more diagnostically relevant scores related to at least one diagnosis of the patient;
   wherein determining the representative ECG trace comprises identifying a subset of the plurality of corresponding sensed ECG trace segments, the subset excluding at least one of the plurality of corresponding sensed ECG trace segments, and determining the representative ECG trace based on the identified subset; and
   wherein identifying the subset of the plurality of corresponding sensed ECG trace segments includes:
      applying principal component analysis to the plurality of corresponding sensed ECG trace segments to determine a respective set of principal component scores associated with each of the corresponding sensed ECG trace segments; and
      comparing the principal component scores to identify the at least one of the plurality of corresponding sensed ECG trace segments to be excluded from the subset.

2. The method of claim 1 wherein each of the sets of principal component scores includes a first principal component score and a second principal component score and wherein comparing the principal component scores comprises:
   determining a first confidence limit and a second confidence limit from the first and second principal component scores respectively; and
   for each of the corresponding sensed ECG trace segments, comparing the first and second principal component scores associated with the sensed ECG trace segment to the first and second confidence limits.

3. The method of claim 2 wherein comparing the first and second principal component scores associated with the sensed ECG trace segment to the first and second confidence limits comprises determining whether the first and second principal component scores are outside of an ellipse having a radius set by the first and second confidence limits, and if so, identifying the sensed ECG trace segment to be excluded from the subset.

4. The method of claim 2 wherein determining the first and second confidence limits comprises applying the Hotelling T2 statistic to the first and second principal component scores respectively.

5. The method of claim 4 wherein applying the Hotelling T2 statistic to the first and second principal component scores comprises using the critical value of the F-distribution at at least about 95% confidence.

6. The method of claim 1 wherein determining the representative ECG trace based on the at least one of the identified corresponding sensed ECG trace segments comprises averaging the corresponding sensed ECG trace segments included in the subset.

7. The method of claim 1 wherein identifying the plurality of corresponding sensed ECG trace segments comprises identifying respective common features in the sensed ECG trace segments and identifying respective start and end times for each of the plurality of sensed ECG trace segments relative to the identified common features.

8. The method of claim 7 wherein identifying the respective common features comprises identifying respective R peaks in each of the sensed ECG trace segments.

9. The method of claim 1 further comprising producing signals representing the one or more diagnostically relevant scores for causing at least one display to display a representation of the one or more diagnostically relevant scores.

10. The method of claim 1 wherein the at least one neural network classifier includes a BrS neural network classifier.

11. The method of claim 1 further comprising training the at least one neural network classifier, the training comprising:
   receiving a plurality of sets of training ECG traces, wherein each set of the sets of training ECG traces represents sensed heart activity over a training time period for a respective associated training patient of a plurality of training patients;
   receiving, for each set of the plurality of sets of training ECG traces, a respective diagnosis for the training patient associated with the set of training ECG traces;
   for each of the training ECG traces:
      identifying a plurality of corresponding training ECG trace segments, each of the training ECG trace segments representing patient heart activity over a segment of the training time period; and
      determining a representative training ECG trace based on at least one of the identified corresponding training ECG trace segments; and
   causing the at least one neural network classifier to be trained using the representative training ECG traces and the diagnoses.

12. A system for facilitating electrocardiogram ("ECG") analysis comprising at least one processor configured to perform the method of claim 1.

13. A non-transitory computer readable medium having stored thereon codes which when executed by at least one processor cause the at least one processor to perform the method of claim 1.

14. A computer-implemented method of facilitating electrocardiogram ("ECG") analysis, the method comprising:
   receiving a plurality of sets of training ECG traces, wherein each set of the sets of training ECG traces represents sensed heart activity over a training time period for a respective associated training patient of a plurality of training patients;

receiving, for each set of the plurality of sets of training ECG traces, a respective diagnosis for the training patient associated with the set of training ECG traces;

for each of the training ECG traces:
identifying a plurality of corresponding training ECG trace segments, each of the training ECG trace segments representing patient heart activity over a segment of the training time period; and
determining a representative training ECG trace based on at least one of the identified corresponding training ECG trace segments; and causing at least one neural network classifier to be trained using the representative training ECG traces and the diagnoses, the at least one neural network classifier configured to output one or more diagnostically relevant scores related to at least one diagnosis;

wherein determining the representative training ECG trace comprises identifying a subset of the plurality of corresponding training ECG trace segments, the subset excluding at least one of the plurality of corresponding training ECG trace segments, and determining the representative training ECG trace based on the identified subset; and wherein identifying the subset of the plurality of corresponding training ECG trace segments includes:
applying principal component analysis to the plurality of corresponding training ECG trace segments to determine a respective set of principal component scores associated with each of the corresponding training ECG trace segments; and
comparing the principal component scores to identify the at least one of the plurality of corresponding training ECG trace segments to be excluded from the subset.

15. The method of claim 14 wherein each of the sets of principal component scores includes a first principal component score and a second principal component score and wherein comparing the principal component scores comprises:
determining a first confidence limit and a second confidence limit from the first and second principal component scores respectively; and
for each of the corresponding training ECG trace segments, comparing the first and second principal component scores associated with the training ECG trace segment to the first and second confidence limits.

16. The method of claim 15 wherein comparing the first and second principal component scores associated with the training ECG trace segment to the first and second confidence limits comprises determining whether the first and second principal component scores are outside of an ellipse having a radius set by the first and second confidence limits, and if so, identifying the training ECG trace segment to be excluded from the subset.

17. The method of claim 15 wherein determining the first and second confidence limits comprises applying a Hotelling T2 statistic equation to the first and second principal component scores respectively.

18. The method of claim 17 wherein applying the Hotelling T2 statistic equation to the first and second principal component scores comprises using the critical value of the F-distribution at at least about 95% confidence.

19. The method of claim 14 wherein determining the representative ECG trace based on the at least one of the identified corresponding training ECG trace segments comprises averaging the corresponding training ECG trace segments included in the subset.

20. The method of claim 14 wherein identifying the plurality of corresponding training ECG trace segments comprises identifying respective common features in the training ECG trace segments and identifying respective start and end times for each of the plurality of training ECG trace segments relative to the identified common features.

21. The method of claim 20 wherein identifying the respective common features comprises identifying respective R peaks in each of the training ECG trace segments.

22. The method of claim 14 wherein the at least one neural network classifier includes a BrS neural network classifier and wherein each of the diagnoses received includes a BrS diagnoses.

23. A system for facilitating electrocardiogram ("ECG") analysis comprising at least one processor configured to perform the method of claim 14.

24. A non-transitory computer readable medium having stored thereon codes which when executed by at least one processor cause the at least one processor to perform the method of claim 14.

* * * * *